(12) United States Patent
Chen et al.

(10) Patent No.: US 11,062,489 B2
(45) Date of Patent: Jul. 13, 2021

(54) SYSTEM AND METHOD FOR MULTI-ARCHITECTURE COMPUTED TOMOGRAPHY PIPELINE

(71) Applicant: Wisconsin Alumni Research Foundation, Madison, WI (US)

(72) Inventors: Guang-Hong Chen, Madison, WI (US); Yinsheng Li, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 214 days.

(21) Appl. No.: 16/275,129

(22) Filed: Feb. 13, 2019

(65) Prior Publication Data

US 2019/0251713 A1 Aug. 15, 2019

Related U.S. Application Data

(60) Provisional application No. 62/630,138, filed on Feb. 13, 2018.

(51) Int. Cl.
*G06T 11/00* (2006.01)
*A61B 6/00* (2006.01)
*G06N 7/00* (2006.01)
*G06N 20/20* (2019.01)
*G06N 3/08* (2006.01)

(52) U.S. Cl.
CPC .......... *G06T 11/006* (2013.01); *A61B 6/5205* (2013.01); *G06N 3/084* (2013.01); *G06N 7/005* (2013.01); *G06N 20/20* (2019.01); *G06T 2210/41* (2013.01)

(58) Field of Classification Search
CPC .............................. G06T 11/006; G06N 20/20
See application file for complete search history.

(56) References Cited

U.S. PATENT DOCUMENTS

2018/0293762 A1* 10/2018 Fu .......................... G06T 11/006
2019/0108441 A1* 4/2019 Thibault .............. G01N 23/046

OTHER PUBLICATIONS

Shen, C. et al, "Intelligent parameter tuning in optimization-based iterative ct reconstruction via deep reinforcement learning." IEEE Trans. Med. Imaging, vol. 37, No. 6, pp. 1430-1439, 2018.
Siddon R.L., "Fast calculation of the exact radiological path for a three-dimensional ct array," Med Phys, vol. 12, No. 2, pp. 252-255, 1985. [Online]. Available: https://www.ncbi.nlm.nih.gov/pubmed/4000088.

(Continued)

*Primary Examiner* — Tuan H Nguyen
(74) *Attorney, Agent, or Firm* — Quarles & Brady LLP

(57) ABSTRACT

A system and method for reconstructing an image of a subject acquired using a tomographic imaging system includes at least one computer processor configured to form an image reconstruction pipeline. The reconstruction pipeline at least includes an automated correction module configured to receive imaging data acquired from a subject using ionizing radiation generated by the tomographic imaging system and generate corrected data using a first learning network. The reconstruction pipeline also includes an intelligent reconstruction module configured to receive at least one of the imaging data and the corrected data and reconstruct an image of the subject using a second learning network.

23 Claims, 8 Drawing Sheets

(56) References Cited

OTHER PUBLICATIONS

Silver, D. et al. Mastering the game of Go with deep neural networks and tree search. Nature 529, 484-503 (2016).
Silver, D. et al. Mastering the game of Go without human knowledge. Nature 550, 354, doi:10.1038/nature24270 (2017).
Syben, C. et al, "A deep learning approach for reconstruction filter kernel discretization," arXiv preprint arXiv:1710.06287, 2017.
Van Nieuwenburg, E.P.L. et al, Learning phase transitions by confusion. Nature Physics 13, 435, doi:10.1038/nphys4037 (2017).
Wang, G. et al, "Image reconstruction is a new frontier of machine learning," IEEE Trans Med Imaging, vol. 37, No. 6, pp. 1289-1296, 2018. [Online]. Available: https://www.ncbi.nlm.nih.gov/pubmed/29870359.
Wolterink, J. M. et al, "Generative adversarial networks for noise reduction in low-dose ct," IEEE transactions on medical imaging, vol. 36, No. 12, pp. 2536-2545, 2017.
Wu, D. et al, "Iterative low-dose ct reconstruction with priors trained by artificial neural network," IEEE transactions on medical imaging, vol. 36, No. 12, pp. 2479-2486, 2017.
Wurfl, T. et al , "Deep learning computed tomography: Learning projection-domain weights from image domain in limited angle problems," IEEE transactions on medical imaging, vol. 37, No. 6, pp. 1454-1463, 2018.
Xie, S. et al. Artifact Removal using Improved GoogLeNet for Sparse-view CT Reconstruction. Sci Rep 8, 6700, doi:10.1038/s41598-018-25153-w (2018).
Yang, Q. et al, "Low dose ct image denoising using a generative adversarial network with wasserstein distance and perceptual loss," IEEE transactions on medical imaging, 2018.
Ye, D.H. et al, "Deep back projection for sparse-view ct reconstruction," arXiv preprint arXiv:1807.02370, 2018.
Ye, Y. et al, A general local reconstruction approach based on a truncated hilbert transform. Int J Biomed Imaging 2007, 63634, doi:10.1155/2007/63634 (2007).
Yi, X. et al. Sharpness-Aware Low-Dose CT Denoising Using Conditional Generative Adversarial Network. J Digit Imaging, doi:10.1007/s10278-018-0056-0 (2018).
Yu H. et al, "Compressed sensing based interior tomography," Phys Med Biol, vol. 54, No. 9, pp. 2791-2805, 2009. [Online]. Available: https://www.ncbi.nlm.nih.gov/pubmed/19369711.
Zhang Y. et al, "Convolutional neural network based metal artifact reduction in x-ray computed tomography," IEEE transactions on medical imaging, vol. 37, No. 6, pp. 1370-1381, 2018.
Zhang, Y. et al, "Low-dose lung ct image restoration using adaptive prior features from full-dose training database," IEEE transactions on medical imaging, vol. 36, No. 12, pp. 2510-2523, 2017.
Zhang, Z. et al, "A sparse-view ct reconstruction method based on combination of densenet and deconvolution." IEEE transactions on medical imaging, vol. 37, No. 6, pp. 1407-1417, 2018.
Zheng, X. et al, "Pwls-ultra: An efficient clustering and learning-based approach for low-dose 3d ct image reconstruction," IEEE transactions on medical imaging, vol. 37, No. 6, pp. 1498-1510, 2018.
Zhu, B., et al. Image reconstruction by domain-transform manifold learning. Nature 555, 487, doi:10.1038/nature25988 (2018).
Zhuang, T. et al. New families of exact fan-beam and cone-beam image reconstruction formulae via filtering the backprojection image of differentiated projection data along singly measured lines. Inverse Problems 22, 991 (2006).
Zhuang, T., et al. Fan-beam and cone-beam image reconstruction via filtering the backprojection image of differentiated projection data. Phys Med Biol 49, 5489-5503 (2004).
Zou, Y. et al, "Image reconstruction in regions-of-interest from truncated projections in a reduced fan-beam scan," Phys Med Biol, vol. 50, No. 1, pp. 13-27, 2005. [Online]. Available: https://www.ncbi.nlm.nih.gov/pubmed/15715419.
Abadi, M. et al, "Tensorflow: Large-scale machine learning on heterogeneous systems," 2015. [Online]. Available: http://tensorflow.org/.
Adler J. et al, "Learned primal-dual reconstruction," IEEE transactions on medical imaging, vol. 37, No. 6, pp. 1322-1332, 2018.
Bengio, Y. Machines Who Learn. Sci Am 314, 46-51, doi:10.1038/scientificamerican0616-46 (2016).
Candes, E. J., et al. Robust uncertainty principles: exact signal reconstruction from highly incomplete frequency information. IEEE Transactions on Information Theory 52, 489-509, doi:10.1109/TIT.2005.862083 (2006).
Chen B. et al, "Statistical iterative cbct reconstruction based on neural network," IEEE transactions on medical imaging, vol. 37, No. 6, pp. 1511-1521, 2018.
Chen H., et al, "Learn: Learned experts assessment-based reconstruction network for sparse-data ct," IEEE transactions on medical imaging, 2018.
Chen H., et al, "Low-does ct with a residual encoder-decoder convolutional neural network," IEEE transactions on medical imaging, vol. 36, No. 12, pp. 2524-2535, 2017.
Chen, G. H. A new framework of image reconstruction from fan beam projections. Med Phys 30, 1151-1161, doi:10.1118/1.1577252 (2003).
Chen, G. H. et al, Development and evaluation of an exact fan-beam reconstruction algorithm using an equal weighting scheme via locally compensated filtered backprojection (LCFBP). Medical Physics 33, 475-481, doi:doi:10.1118/1.2165416 (2006).
Chollet F., "Keras," 2015. [Online]. Available: https://keras.io.
Clackdoyle R. et al, "Tomographic reconstruction in the 21st century," IEEE Signal Processing Magazine, vol. 27, No. 4, pp. 60-80, 2010.
Clackdoyle R. et al, A large class of inversion formulae for the 2D Radon transform of functions of compact support. Inverse Problems 20, 1281 (2004).
Cybenko G. et al., Approximation by superpositions of sigmodial function. Mathematics of Control, Signals and Systems 2, 303-314 (1989).
Donoho, D. L. Compressed sensing. IEEE Transactions on Information Theory 52, 1289-1306, doi:10.1109/TIT.2006.871582 (2006).
Garrett, J. W. et al, "Reduced anatomical clutter in digital breast tomosynthesis with statistical iterative reconstruction," Medical physics, vol. 45, No. 5, pp. 2009-2022, 2018.
Ge, Y. et al, "Deconvolution-based backproject-filter (bpf) computed tomography image reconstruction method using deep learning technique," arXiv preprint arXiv:1807.01833, 2018.
Ghahramani, Z. Probabilistic machine learning and artificial intelligence. Nature 521, 452, doi:10.1038/nature14541 (2015).
Glorot, X. et al. Understanding the difficulty of training deep feedforward neural networks. In Proceedings of the thirteenth international conference on artificial intelligence and statistics (pp. 249-256). 2010.
Gupta, H. et al, "Cnn-based projected gradient descent for consistent ct image reconstruction," IEEE transactions on medical imaging, vol. 37, No. 6, pp. 1440-1453, 2018.
Han Y. et al, "Framing u-net via deep convolutional framelets: Application to sparse-view ct," IEEE transactions on medical imaging, vol. 37, No. 6, 1418-1429, 2018.
Han, S., et al. "Learning both weights and connections for efficient neural network." Advances in neural information processing systems. 2015.
Han, Y. et al, "Deep learning interior tomography for region-of-interest reconstruction," arXiv preprint arXiv:1712.10248, 2017.
Han, Y. et al, "Deep learning reconstruction for 9-view dual energy ct baggage scanner," arXiv preprint arXiv:1801.01258, 2018.
Han, Y.S. et al, "Deep residual learning for compressed sensing ct reconstruction via persistent homology analysis," arXiv preprint arXiv:1611.06391, 2016.
Hornik K., Approximation capabilities of multilayer feedforward networks. Neural Networks 4, 251-257, doi:10.1016/0893-6080(91)90009-t (1991).
Jin, K. H. et al, "Deep convolutional neural network for inverse problems in imaging," IEEE Transactions on Image Processing, vol. 26, No. 9, pp. 4509-4522, 2017.
Jordan, M. I. et al. Machine learning: Trends, perspectives, and prospects. Science 349, 255-260, doi:10.1126/science.aaa8415 (2105).

(56) References Cited

OTHER PUBLICATIONS

Kang, E. et al, "Cycle-consistent adversarial denoising network for multiphase coronary ct angiography," Medical physics, 2018.
Kang, E. et al, "Deep convoluctional framelet denosing for low-dose ct via wavelet residual network," IEEE transactions on medical imaging, vol. 37, No. 6, pp. 1358-1369, 2018.
Kang, E., et al. A deep convoluctional neural network using directional wavelets for low-dose X-ray CT reconstruction. Med Phys 44, e360-e375, doi:10.1002/mp.12344 (2017).
Kelly, B. et al, "Deep learning-guided image reconstruction from incomplete data," arXiv preprint arXiv:1709.00584, 2017.
Kingma D. et al , "Adam: A method for stochastic optimization," arXiv preprint arXiv:1412.6980 , 2014.
Kingma, D. P. et al. "Adam: A method for stochastic gradient descent." ICLR: International Conference on Learning Represenations. 2015.
Kudo, H., et al. Tiny a priori knowledge solves the interior problem in computed tomography. Phys Med Biol 53, 2207-2231, doi:10.1088/0031-9155/53/9/001 (2008).
Lecun, Y., et al. "Handwritten zip code recognition with multilayer networks." [1990] Proceedings. 10th International Conference on Pattern Recognition. vol. 2. IEEE, 1990.
Lecun, Y., et al. Deep learning. Nature 521, 436-444, doi:10.1038/nature14539 (2015).
Lee, H. et al, "Deep-neural-network based sinogram synthesis for sparse-view ct image reconstruction," arXiv preprint arXiv:1803.00694, 2018.
Li, K. et al, "Statistical model based iterative reconstruction (MBIR) in clinical CT systems: Experimental assessment of noise performance," Medical physics 41(4), p. 041906, 2014.
Mnih, V. et al. Human-level control through deep reinforcement learning. Nature 518, 529-533, doi:10.1038/nature14236 (2015).
Noo, F. et al, A two-step Hilbert transform method for 2D image reconstruction. Phys Med Biol 49, 3903-3923 (2004).
Noo, F. et al, Image reconstruction from fan-beam projections on less than a short scar. Phys Med Biol 47, 2525-2546 (2002).
Park, H.S. et al, "Ct sinogram-consistency learning for metal-induced beam hardening correction," Medical physics, vol. 45, No. 12, pp. 5376-5384, 2018.
Pickhardt, P. J. et al, "Abdominal CT with model-based iterative reconstruction (MBIR): initial results of a prospective trial comparing ultralow-dose with standard-dose imaging," American journal of roentgenology 199(6), pp. 1266-1274, 2012.
Pooler, B.D. et al, "Prospective Evaluation of Reduced Dose Computed Tomography for the Detection of Low-Contrast Liver Lesions: Direct Comparison with Concurretn Standard Dose Imaging," European Radiology, pp. 1-12, 2016.
Radon, J. On the Determination of Functions from Their Integral Values along Certain Manifolds. IEEE Trans Med Imaging 5, 170-176, doi:10.1109/tmi.1986.4307775 (1986).
Rumelhart, D. E. et al. "Learning representations by back-propagating errors." nature 323.6088 (1986): 533-536.
Schmidhuber J., "Deep learning in neural networks: An overview," Neural Networks, vol. 61, pp. 85-117, 2015. [Online]. Available: http://www.sciencedirect.com/science/article/pii/S0893608014002135.
Schoenholz, S. S., et al. A structural approach to relaxation in glassy liquids. Nature Physics 12, 469, doi:10.1038/nphys3644 (2016).
Segler, M. H. S., et al. Planning chemical syntheses with deep neural networks and symbolic AI. Nature 555, 604-610, doi:10.1038/nature25978 (2018).
Shan, H. et al, "3-d convolutional encoder-decoder network for low-dose ct via transfer learning from a 2-d trained network," IEEE transactions on medical imaging, vol. 37, No. 6, pp. 1522-1534, 2018.

* cited by examiner

SYSTEM AND METHOD FOR MULTI-ARCHITECTURE COMPUTED TOMOGRAPHY PIPELINE

CROSS-REFERENCE

This application is based on, claims priority to, and incorporates herein by reference in its entirety, U.S. Provisional Application Ser. No. 62/630,138, filed Feb. 13, 2018, and entitled, "SYSTEM AND METHOD FOR MULTI-ARCHITECTURE COMPUTED TOMOGRAPHY PIPELINE."

STATEMENT REGARDING FEDERALLY SPONSORED RESEARCH

This invention was made with government support under EB021183 and EB020521 awarded by the National Institutes of Health. The government has certain rights in the invention.

BACKGROUND

The present disclosure relates to systems and methods for medical image data preparation and/or reconstruction. More particularly, systems and method are provided for generating medical images with greater efficiency, less artifacts, and/or greater information and flexibility than traditional reconstruction systems.

With conventional image reconstruction techniques, such as filtered backprojection for multi-detector CT (MDCT) or C-arm cone beam CT (CBCT) imaging, individual images are reconstructed from a corresponding set of data acquired with the medical imaging system. For example, one image is reconstructed from a single sinogram in x-ray MDCT, CBCT imaging. The dominant framework for CT image reconstruction is filtered backprojection (FBP). Though well-understood and widely-adopted, FBP suffers from some inherent limitations and, thus, many efforts have been made to control the shortcomings of traditional CT hardware and the reconstruction of FBP. However, each of these efforts raises the complexity of the reconstruction pipeline and, in many cases, creates new challenges when attempting to control against old challenges.

For example, the ionizing radiation delivered to patients during CT imaging has been shown to be a potential mechanism of carcinogenesis. Hence, many have worked to develop hardware, software, and imaging protocols to lower radiation dose, while still maintaining the image quality required for clinical analysis. X-ray tube current reduction is considered as one practical way to reduce the radiation dose. However, a reduction in detected x-ray fluence lowers the signal-to-noise ratio in the projection data and, thus, increases the noise in the reconstructed images, if conventional FBP is used for reconstruction.

The constraints of managing the signal-to-noise ratio is exacerbated if the material composition or geometrical shape of the image object causes severe photon starvation in specific line integrals at certain view angles. This local and directional photon starvation effect can be referred to as the challenges associated with low photon counts. The result of these low photon counts can be severe, bright, oriented noise streaks in FBP images. These challenges are in addition to the well-known elevation of noise amplitude associated with radiation dose reduction. These structured artifacts are most commonly found for rays of measurement passing through highly attenuating tissues, such as bones or contrast-enhanced ventricles. Such severe artifacts may decrease image quality, obscure anatomy, and create bias in tissue attenuation values.

Various strategies have been proposed to reduce the excessive image noise and streaks in low dose FBP images. These efforts can be categorized according to the stage of the CT imaging chain within which they are designed to operate. There are low signal correction methods, applied before the log-transform is taken. There are also sinogram smoothing methods, which are applied after the log-transform but before image reconstruction. Furthermore, there are model based image reconstruction (MBIR) methods, which penalize the data with high noise by assigning a lower weight in image reconstruction and incorporate the desired image smoothness into the regularization process of image reconstruction such that the noise amplitude and noise streaks can be reduced in the reconstructed images. Furthermore, there are post-processing methods that operate after image reconstruction to attempt to correct such issues after the image has been reconstructed.

Recently, major CT manufacturers have commercialized proprietary, low-signal correction (LSC) and MBIR techniques for clinical use. These new techniques offer significant potential to reduce CT image noise and, thus, enable clinicians and medical physicists to lower radiation dose in CT exams. However, in the process of translating these techniques into clinical practice, quantitative image quality assessments have revealed several unfavorable properties compared to the well understood FBP method. These include but are not limited to the fact that spatial resolution is dependent on location, image contrast, and radiation dose levels. As such, for high-contrast image objects, the edges of an MBIR reconstructed image can be sharper than that of the FBP reconstructed image, whereas, for a low-contrast image objects, the FBP image may be sharper than the MBIR image. Another unfavorable property is reflected in the fact that the noise power spectrum (NPS) structure has a strong dependence on dose level, in contrast to FBP methods, where the dose-normalized NPS structure depends on the selected image reconstruction kernel, but not on the dose level. Additionally, the peak frequency of the NPS of an MBIR reconstruction shifts towards the lower spatial frequency end as the radiation dose is lowered, unlike the dose-invariant peak frequency of an FBP NPS.

In the clinical translation of these new technologies, a key question is whether an appropriate radiation dose level can be prescribed for a specific imaging task without loss of diagnostic image quality. When these new technologies are directly applied to clinical CT exams based upon the noise reduction magnitude, recent clinical studies have shown that the clinical diagnostic performance of these new MBIR reconstruction techniques is somewhat limited. The currently limited diagnostic performance may be attributed, at least partially, to the above undesirable and difficult-to-control properties of current MBIR methods.

Thus, a need persists to improve upon current CT image acquisition, reconstruction, and/or post-processing paradigms.

SUMMARY

The present disclosure overcomes the aforementioned drawbacks by providing a new paradigm for CT data correction and reconstruction. In particular, the present disclosure provides systems and methods that utilize a multi-stage cascaded network architecture with interpretable stages to achieve interpretable and tunable functional modules. Some functional modules may include an intelligent correction module and an intelligent reconstruction module. Others may, optionally, include a virtual radiologist module to judge the image quality and send feedbacks to the previous modules to fine tune the data correction and image reconstruction modules. These functional modules created by the multiple interpretable stages presents a reconstruction pipeline that can replace traditional, commercial tomographic reconstruction pipelines, or just portions of a given traditional, commercial tomographic reconstruction pipeline. Thus the present disclosure provides new paradigm for CT data correction and reconstruction that is flexible and readily designed for deployment to replace or accompany portions of a traditional reconstruction pipeline.

In accordance with one aspect of the disclosure, a system for reconstructing an image of a subject acquired using a tomographic imaging system is provided. The system includes at least one computer processor configured to form an image reconstruction pipeline at least including an automated correction module configured to receive imaging data acquired from a subject using ionizing radiation generated by the tomographic imaging system and generate corrected data using a first learning network. The reconstruction pipeline also includes an intelligent reconstruction module configured to receive at least one of the imaging data and the corrected data and reconstruct an image of the subject using a second learning network. The system further includes a display configured to display the image of the subject.

In accordance with another aspect of the disclosure, a computed tomography (CT) system is provided that includes an x-ray source and associated detectors configured to acquire imaging data from a subject over a range of view angles. The system also includes a computer system including at least one processor configured to operate as an automated correction module configured to receive imaging data acquired from a subject using the x-ray source and associated detectors and generate corrected data using a first learning network. The at least one processor is further configured to operate as an intelligent reconstruction module configured to receive at least one of the imaging data and the corrected data and reconstruct an image of the subject using a second learning network. The system also includes a display configured to display the image of the subject.

In accordance with yet another aspect of the disclosure, a computed tomography (CT) system is disclosed that includes an x-ray source and associated detectors configured to acquire imaging data from a subject over a range of view angles and a computer system. The computer system includes at least one processor configured to operate as an automated correction module configured to receive imaging data acquired from a subject using the x-ray source and associated detectors and generate corrected data using a first learning network and a reconstruction module configured to receive the corrected data and reconstruct an image of the subject using at least the corrected data. The system also includes a display configured to display the image of the subject.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
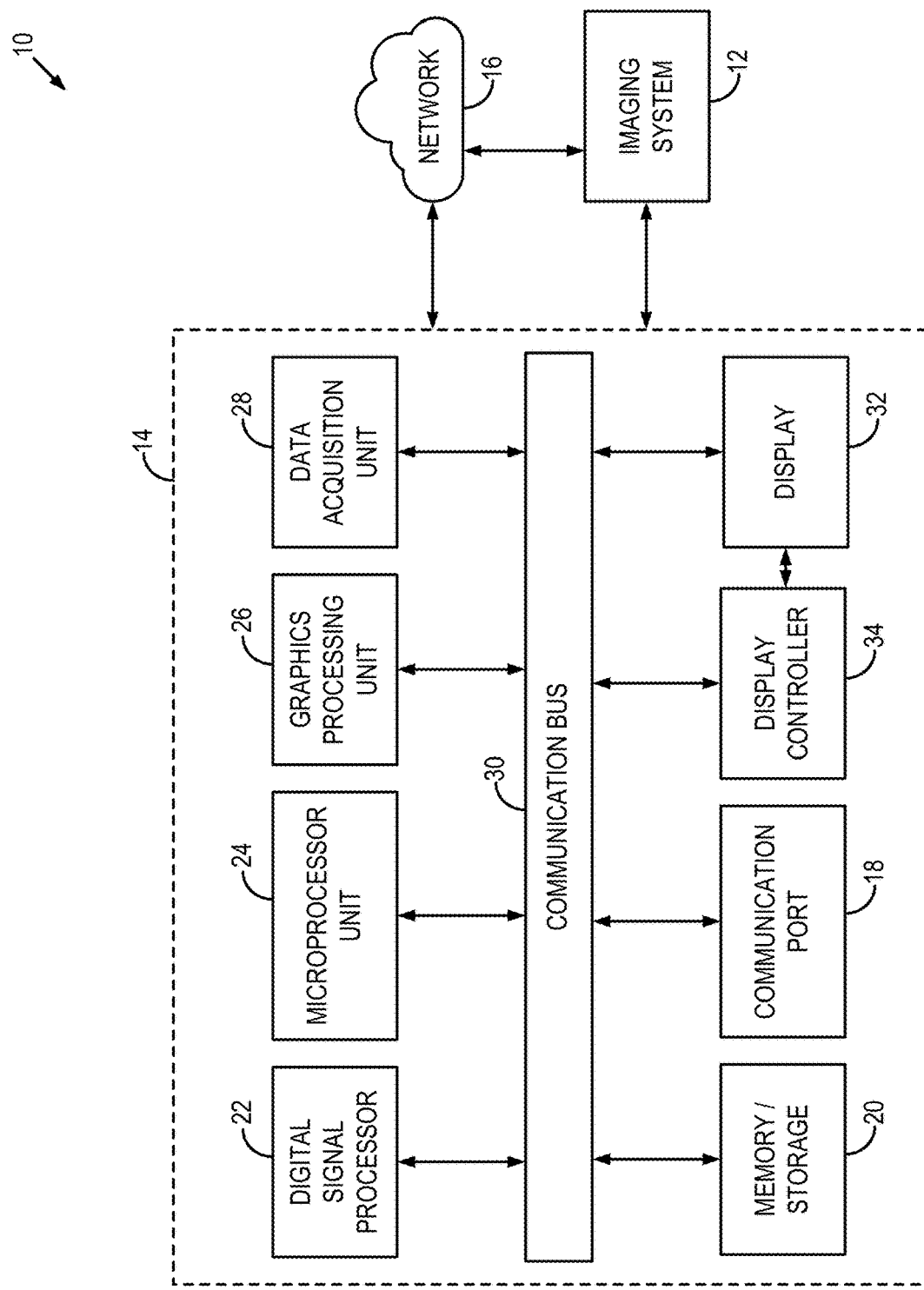
FIG. 1 is a schematic diagram of an example computer system that can be configured to implement the methods described herein.

The reconstruction of a function in N-dimensional space from its integral values over a K-dimensional hyperplane ($1 \leq K < N$) is a central topic in integral geometry. The importance of integral geometry in our daily life can be appreciated by noting that the data acquired in x-ray medical computed tomography (CT) are essentially line integrals through the human body. The line integral data (i.e., integral values for $K=1$) is acquired at different view angles as the tube-detector assembly rotates from one angular position to another. Image reconstruction from line integrals is also central to other imaging modalities, such as single photon emission computed tomography (SPECT) and positron Emission tomography (PET). Thus, though a non-limiting example of CT imaging systems is provided, the systems and methods provided herein are not limited to a CT imaging and may be extended to other modalities.

In an ideal scenario, when acquired line integral data can be converted to properly fill the corresponding Fourier space of the image function, the modern filtered back projection (FBP) solution can be readily derived using the inverse Fourier transform, essentially equivalent to the one discovered by Radon in 1917. However, the Fourier transform related FBP reconstruction method is rather restrictive. Due to the quasi-local nature of the information encoding process (i.e., the acquisition of line integral data only involves the function values along a straight line) as well as the use of divergent beam acquisition geometry in CT, there are many other new solutions to exactly reconstruct the image function. Interestingly, these solutions are not mathematically equivalent to one another and these new solutions even enable one to accurately reconstruct a region of interest (ROI) inside the scan field of view (FOV) with much more relaxed data acquisition conditions (e.g., the super-short scan problem). In this case, it is important to note that there is missing data in Fourier space and; thus, the Fourier-based FBP methods can fail to accurately reconstruct the image. Furthermore, if all of the acquired line integral data is potentially truncated, the intrinsic connection with the Fourier transform of the image object can completely fail. In this so-called interior problem, it can be mathematically proven that a stable solution does exist under certain conditions, albeit no analytical inversion formula has been discovered yet for this case.

The reconstruction problem with line integral data becomes even more difficult when data acquisition view angles are sparse. Despite the so-called compressed sensing (CS) theory having provided a mathematical foundation to address this sparse view reconstruction problem, when the super-short scan and interior problems in CT encounter sparse view acquisitions, it remains unknown whether it is possible to accurately reconstruct either the entire image or local ROIs within the FOV. Additionally, the inevitable noise contamination in data acquisition further complicates image reconstruction problems from line integral data.

As will be described, a new tomographic reconstruction architecture is provided. In one non-limiting implementation, the systems and methods described herein may be used with CT systems. In this non-limiting example, an intelligent CT network (iCT-Net) is provided. Furthermore, as will be described, iCTNet can be trained to solve reconstruction problems with either complete or incomplete line integral data including problems that have not been solved or have not been satisfactorily solved by human knowledge. That is, as will be described, iCT-Net provides a new paradigm to reconstruct CT images for a variety of reconstruction problems under very different conditions within a unified framework. The systems and methods to be described illustrate the capability to accurately reconstruct images for those reconstruction problems that have already been completely solved by human efforts, problems that have been solved only partially by human efforts, and problems that have not been successfully addressed in any meaningful way using human knowledge. Furthermore, though iCT-Net provides one detailed implementations, other generalizations or conceptualizations are provided to integrate with or replace portions or all of traditional image reconstruction pipelines.

Referring now to FIG. 1, a block diagram of an example system 10 is provided that can be configured to carry out techniques, methods, and processes accordance with the present disclosure. The system may include an imaging system 12 that is coupled to a computer system 14. The coupling of the imaging system 12 to the computer system 14 may be a direct or dedicated network connection, or may be through a broad network 16, such as an intranet or the Internet.

The computer system 14 may be a workstation integrated with or separate from the medical imaging systems 12 or a variety of other medical imaging systems, including, as non-limiting examples, computed tomography (CT) system, magnetic resonance imaging (MRI) systems, positron emission tomography (PET) systems, single photon emission computed tomography (SPECT) systems, and the like. Furthermore, the computer system 14 may be a workstation integrated within the medical imaging system 12 or may be a separate workstation or mobile device or computing system. To this end, the following description of particular hardware and configurations of the hardware of the example computer system 14 is for illustrative purposes. Some computer systems may have varied, combined, or different hardware configurations.

Medical imaging data acquired by the medical imaging system 12 or other imaging system can be provided to the computer system 14, such as over the network 16 or from a storage device. To this end, the computer system 14 may include a communications port or other input port 18 for communication with the network 16 and system coupled thereto. Also, the computer system 14 may include memory and storage capacity 20 to store and access data or images.

In some configuration, computer system 14 may include one or more processing systems or subsystems. That is, the computer system 14 may include one or more physical or virtual processors. As an example, the computer system 14 may include one or more of a digital signal processor (DSP) 22, a microprocessor unit (MPU) 24, and a graphics processing unit (GPU) 26. If the computer system 14 is integrated into the medical imaging system, a data acquisition unit 28 may be connected directly to the above-described processor(s) 22, 24, 26 over a communications bus 30, instead of communicating acquired data or images via the network 16. As an example, the communication bus 30 can be a group of wires, or a hardwire used for switching data between the peripherals or between any component, such as the communication buses described above.

The computer system 14 may also include or be connected to a display 32. To this end, the computer system 14 may include a display controller 34. The display 32 may be a monitor connected to the computer system 14 or may be integrated with the computer system 14, such as in portable computers or mobile devices.

Figure 2A:
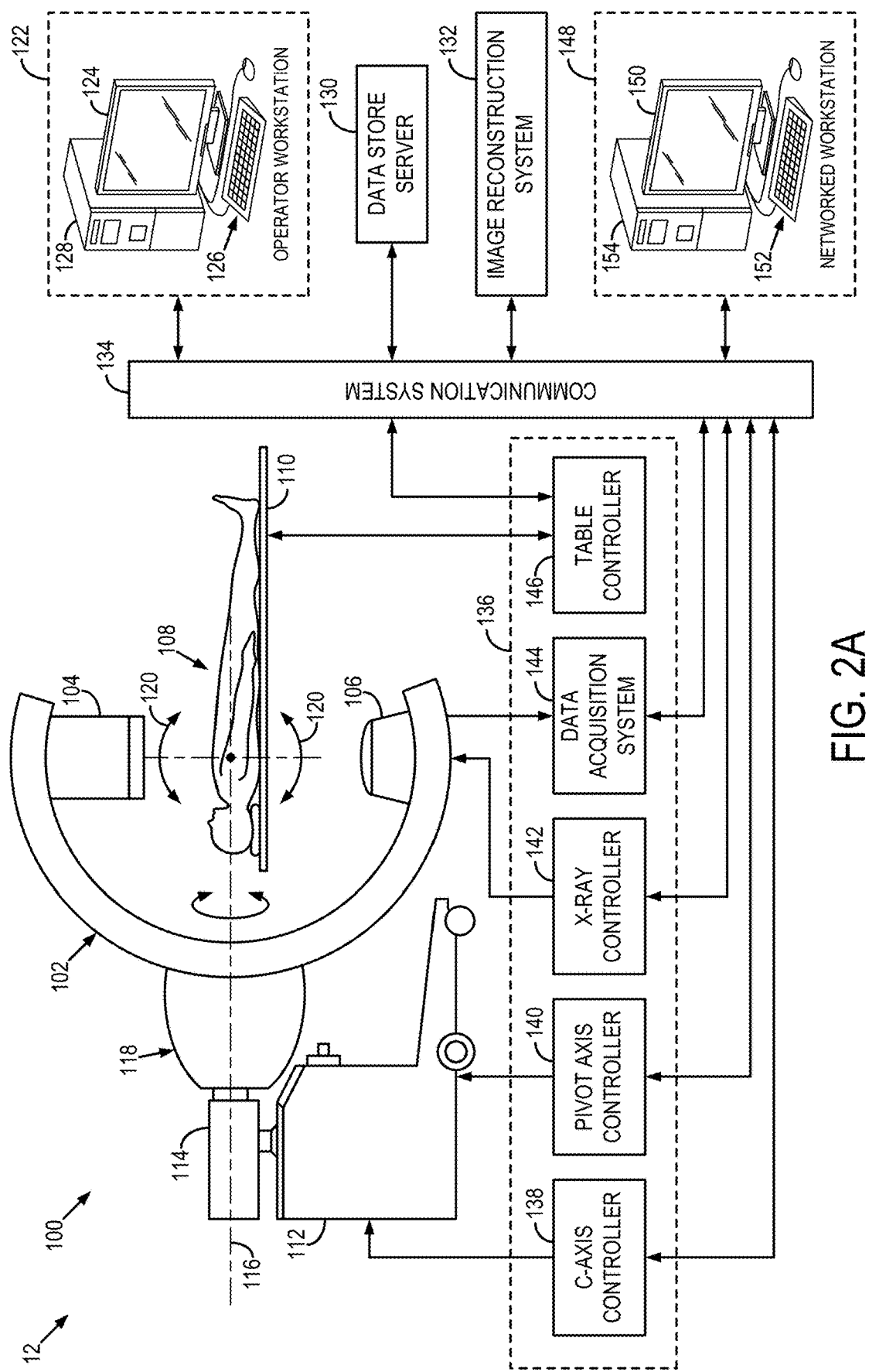
FIG. 2A is a schematic diagram of a C-arm x-ray computed tomography (CT) imaging system configured in accordance with the present disclosure.
Figure 2B:
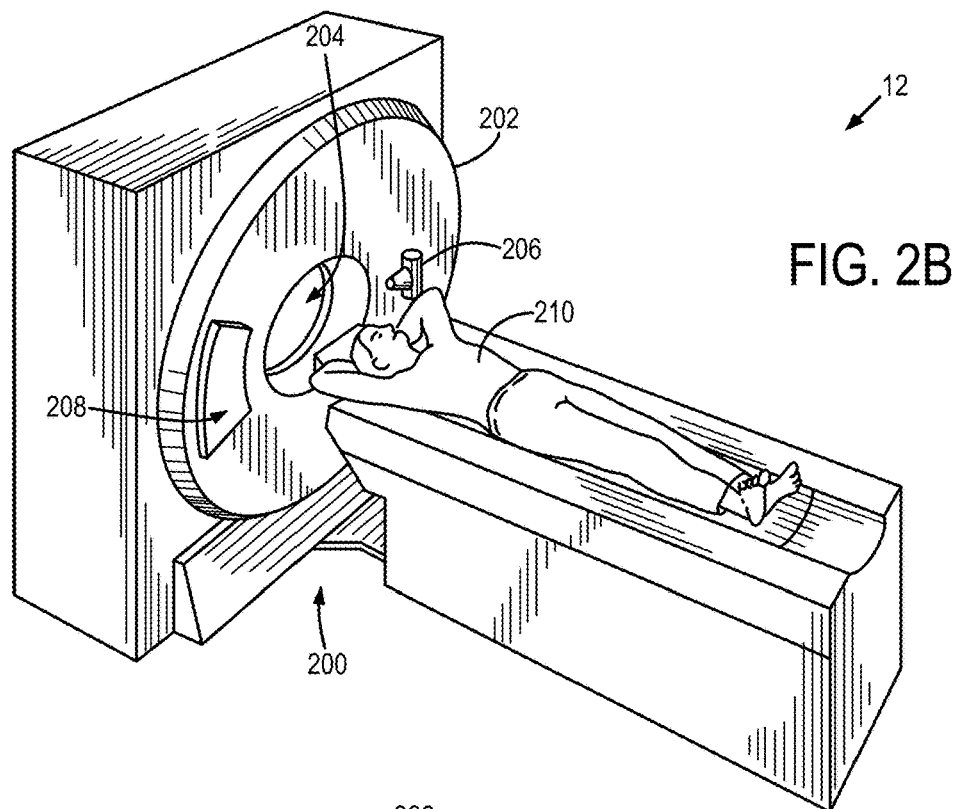
FIG. 2B is a perspective view of an example of an x-ray computed tomography (CT) system.

Referring to FIG. 2A, one, non-limiting example of the imaging system 12 of FIG. 1 is provided. Specifically, in this example, a so-called "C-arm" x-ray imaging system 100 is illustrated for use in accordance with some aspects of the present disclosure. Such an imaging system is generally designed for use in connection with interventional procedures. Such systems stand in contrast to, for example, traditional computed tomography (CT) systems 200, such as illustrated in FIG. 2B, which may also serve as an example of the imaging system 12 of FIG. 1.

Referring again to FIG. 2A, the C-arm x-ray imaging system 100 includes a gantry 102 having a C-arm to which an x-ray source assembly 104 is coupled on one end and an x-ray detector array assembly 106 is coupled at its other end. The gantry 102 enables the x-ray source assembly 104 and detector array assembly 106 to be oriented in different positions and angles around a subject 108, such as a medical patient or an object undergoing examination, which is positioned on a table 110. When the subject 108 is a medical patient, this configuration enables a physician access to the subject 108.

The x-ray source assembly 104 includes at least one x-ray source that projects an x-ray beam, which may be a fan-beam or cone-beam of x-rays, towards the x-ray detector array assembly 106 on the opposite side of the gantry 102. The x-ray detector array assembly 106 includes at least one x-ray detector, which may include a number of x-ray detector elements. Examples of x-ray detectors that may be included in the x-ray detector array assembly 106 include flat panel detectors, such as so-called "small flat panel" detectors. Such a detector panel allows the coverage of a field-of-view of approximately twelve centimeters.

Together, the x-ray detector elements in the one or more x-ray detectors housed in the x-ray detector array assembly 106 sense the projected x-rays that pass through a subject 108. Each x-ray detector element produces an electrical signal that may represent the intensity of an impinging x-ray beam and, thus, the attenuation of the x-ray beam as it passes through the subject 108. In some configurations, each x-ray detector element is capable of counting the number of x-ray photons that impinge upon the detector. During a scan to acquire x-ray projection data, the gantry 102 and the components mounted thereon rotate about an isocenter of the C-arm x-ray imaging system 100.

The gantry 102 includes a support base 112. A support arm 114 is rotatably fastened to the support base 112 for rotation about a horizontal pivot axis 116. The pivot axis 116 is aligned with the centerline of the table 110 and the support arm 114 extends radially outward from the pivot axis 116 to support a C-arm drive assembly 118 on its outer end. The C-arm gantry 102 is slidably fastened to the drive assembly 118 and is coupled to a drive motor (not shown) that slides the C-arm gantry 102 to revolve it about a C-axis, as indicated by arrows 120. The pivot axis 116 and C-axis are orthogonal and intersect each other at the isocenter of the C-arm x-ray imaging system 100, which is indicated by the black circle and is located above the table 110.

The x-ray source assembly 104 and x-ray detector array assembly 106 extend radially inward to the pivot axis 116 such that the center ray of this x-ray beam passes through the system isocenter. The center ray of the x-ray beam can thus be rotated about the system isocenter around either the pivot axis 116, the C-axis, or both during the acquisition of x-ray attenuation data from a subject 108 placed on the table 110. During a scan, the x-ray source and detector array are rotated about the system isocenter to acquire x-ray attenuation projection data from different angles. By way of example, the detector array is able to acquire thirty projections, or views, per second.

The C-arm x-ray imaging system 100 also includes an operator workstation 122, which typically includes a display 124; one or more input devices 126, such as a keyboard and mouse; and a computer processor 128. The computer processor 128 may include a commercially available programmable machine running a commercially available operating system. The operator workstation 122 provides the operator interface that enables scanning control parameters to be entered into the C-arm x-ray imaging system 100. In general, the operator workstation 122 is in communication with a data store server 130 and an image reconstruction system 132. By way of example, the operator workstation 122, data store sever 130, and image reconstruction system 132 may be connected via a communication system 134, which may include any suitable network connection, whether wired, wireless, or a combination of both. As an example, the communication system 134 may include both proprietary or dedicated networks, as well as open networks, such as the Internet.

The operator workstation 122 is also in communication with a control system 136 that controls operation of the C-arm x-ray imaging system 100. The control system 136 generally includes a C-axis controller 138, a pivot axis controller 140, an x-ray controller 142, a data acquisition system ("DAS") 144, and a table controller 146. The x-ray controller 142 provides power and timing signals to the x-ray source assembly 104, and the table controller 146 is operable to move the table 110 to different positions and orientations within the C-arm x-ray imaging system 100.

The rotation of the gantry 102 to which the x-ray source assembly 104 and the x-ray detector array assembly 106 are coupled is controlled by the C-axis controller 138 and the pivot axis controller 140, which respectively control the rotation of the gantry 102 about the C-axis and the pivot axis 116. In response to motion commands from the operator workstation 122, the C-axis controller 138 and the pivot axis controller 140 provide power to motors in the C-arm x-ray imaging system 100 that produce the rotations about the C-axis and the pivot axis 116, respectively. For example, a program executed by the operator workstation 122 generates motion commands to the C-axis controller 138 and pivot axis controller 140 to move the gantry 102, and thereby the x-ray source assembly 104 and x-ray detector array assembly 106, in a prescribed scan path.

The DAS 144 samples data from the one or more x-ray detectors in the x-ray detector array assembly 106 and converts the data to digital signals for subsequent processing. For instance, digitized x-ray data is communicated from the DAS 144 to the data store server 130. The image reconstruction system 132 then retrieves the x-ray data from the data store server 130 and reconstructs an image therefrom. The image reconstruction system 130 may include a commercially available computer processor, or may be a highly parallel computer architecture, such as a system that includes multiple-core processors and massively parallel, high-density computing devices. Optionally, image reconstruction can also be performed on the processor 128 in the operator workstation 122. Reconstructed images can then be communicated back to the data store server 130 for storage or to the operator workstation 122 to be displayed to the operator or clinician.

The C-arm x-ray imaging system 100 may also include one or more networked workstations 148. By way of example, a networked workstation 148 may include a display 150; one or more input devices 152, such as a keyboard and mouse; and a processor 154. The networked workstation 148 may be located within the same facility as the operator workstation 122, or in a different facility, such as a different healthcare institution or clinic.

The networked workstation 148, whether within the same facility or in a different facility as the operator workstation 122, may gain remote access to the data store server 130, the image reconstruction system 132, or both via the communication system 134. Accordingly, multiple networked workstations 148 may have access to the data store server 130, the image reconstruction system 132, or both. In this manner, x-ray data, reconstructed images, or other data may be exchanged between the data store server 130, the image reconstruction system 132, and the networked workstations 148, such that the data or images may be remotely processed by the networked workstation 148. This data may be exchanged in any suitable format, such as in accordance with the transmission control protocol ("TCP"), the Internet protocol ("IP"), or other known or suitable protocols.

Figure 2C:
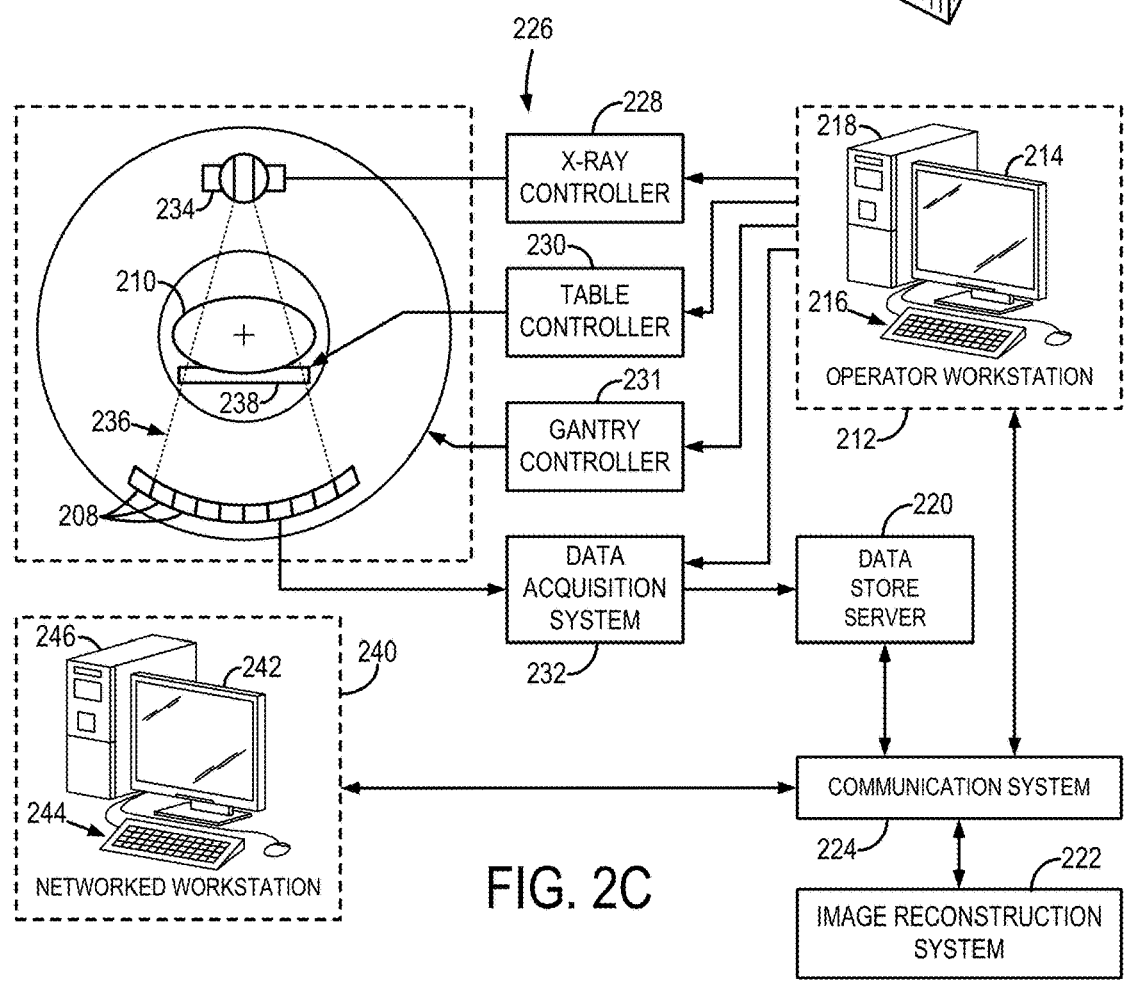
FIG. 2C is a block diagram of CT system, such as illustrated in FIG. 2B.

Similarly, referring to FIGS. 2B and 2C, the imaging system 12 may include a traditional CT system 200, which includes a gantry 202 that forms a bore 204 extending therethrough. In particular, the gantry 202 has an x-ray source 206 mounted thereon that projects a fan-beam, or cone-beam, of x-rays toward a detector array 208 mounted on the opposite side of the bore 204 through the gantry 202 to image the subject 210.

The CT system 200 also includes an operator workstation 212, which typically includes a display 214; one or more input devices 216, such as a keyboard and mouse; and a computer processor 218. The computer processor 218 may include a commercially available programmable machine running a commercially available operating system. The operator workstation 212 provides the operator interface that enables scanning control parameters to be entered into the CT system 200. In general, the operator workstation 212 is in communication with a data store server 220 and an image reconstruction system 222 through a communication system or network 224. By way of example, the operator workstation 212, data store sever 220, and image reconstruction system 222 may be connected via a communication system 224, which may include any suitable network connection, whether wired, wireless, or a combination of both. As an example, the communication system 224 may include both proprietary or dedicated networks, as well as open networks, such as the Internet.

The operator workstation 212 is also in communication with a control system 226 that controls operation of the CT system 200. The control system 226 generally includes an x-ray controller 228, a table controller 230, a gantry controller 231, and a data acquisition system (DAS) 232. The x-ray controller 228 provides power and timing signals to the x-ray module(s) 234 to effectuate delivery of the x-ray beam 236. The table controller 230 controls a table or platform 238 to position the subject 210 with respect to the CT system 200.

The DAS 232 samples data from the detector 208 and converts the data to digital signals for subsequent processing. For instance, digitized x-ray data is communicated from the DAS 232 to the data store server 220. The image reconstruction system 222 then retrieves the x-ray data from the data store server 220 and reconstructs an image therefrom. The image reconstruction system 222 may include a commercially available computer processor, or may be a highly parallel computer architecture, such as a system that includes multiple-core processors and massively parallel, high-density computing devices. Optionally, image reconstruction can also be performed on the processor 218 in the operator workstation 212. Reconstructed images can then be communicated back to the data store server 220 for storage or to the operator workstation 212 to be displayed to the operator or clinician.

The CT system 200 may also include one or more networked workstations 240. By way of example, a networked workstation 240 may include a display 242; one or more input devices 244, such as a keyboard and mouse; and a processor 246. The networked workstation 240 may be located within the same facility as the operator workstation 212, or in a different facility, such as a different healthcare institution or clinic.

The networked workstation 240, whether within the same facility or in a different facility as the operator workstation 212, may gain remote access to the data store server 220 and/or the image reconstruction system 222 via the communication system 224. Accordingly, multiple networked workstations 240 may have access to the data store server 220 and/or image reconstruction system 222. In this manner, x-ray data, reconstructed images, or other data may be exchanged between the data store server 220, the image reconstruction system 222, and the networked workstations 212, such that the data or images may be remotely processed by a networked workstation 240. This data may be exchanged in any suitable format, such as in accordance with the transmission control protocol (TCP), the Internet protocol (IP), or other known or suitable protocols.

When x-ray photons interact with an image object to encode the structural information of that object into measured line integral data, quantum noise caused by the intrinsic photon number fluctuations is inherent in the measured data. Therefore, uncertainty is inevitable in the acquired line integral data in x-ray CT and thus it is natural to use a statistical framework to address the image reconstruction problem. In this framework, an image estimate $\hat{x}$ is defined as the image that maximizes the posteriori conditional probability P(x|y) given the measured line integral data y∈Y, where y denotes the individual line integral datum in sinogram space, which is denoted as Y. This can be accomplished via the Bayesian inference and solving the optimization problem given by $\hat{x}$=arg max P (x|y)=arg max P(y|x) P(x).

This method requires an explicit assumption about the a priori distribution P(x). In statistical machine learning, instead of using an explicit assumption on the prior P(x), the posterior distribution P(x|y) is directly learned from the training data via a supervised learning process. In this process, a sample $x_i$ is drawn from the output training image data set and a sample $y_i$ is drawn from the input training line integral data set. The data pairs $(y_i,x_i)$ can be used to train the iCT-Net in this work, to learn a map $f:Y\to X$ (X denotes image space), i.e., a map directly from sinogram space to image space, such that the learned model distribution, Q(x|y; $f$), can best approximate the underlying posterior distribution, P(x|y). Once the map $f:Y\to X$ is learned, it can be applied to predict an image output from the input projection data not used in the training process.

Figure 3:
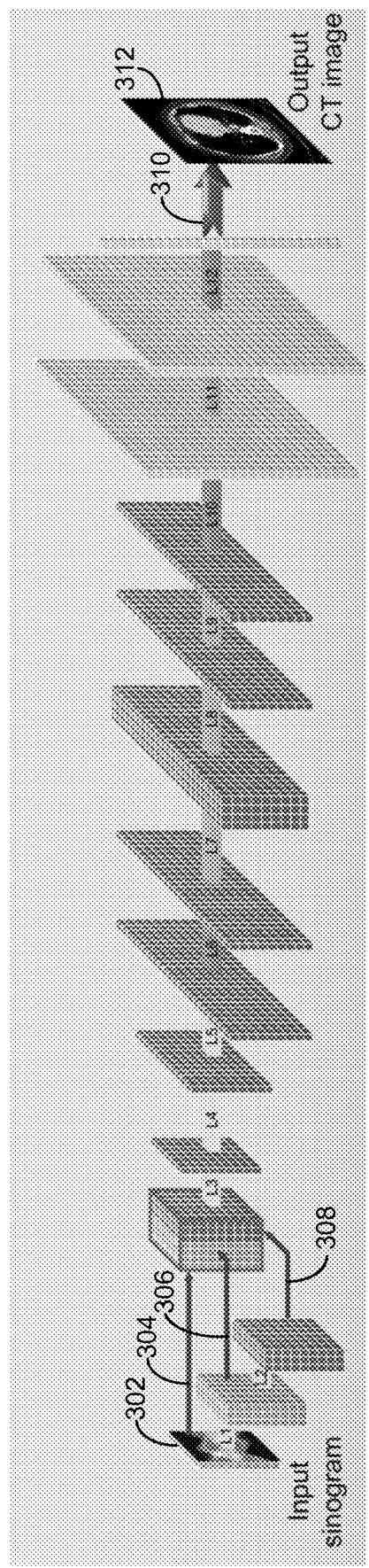
FIG. 3 is a block diagram illustrating one particular implementation for image reconstruction in according to the present disclosure, referred to herein as iCT-Net.

A schematic illustration of the iCT-Net 300 can be conceptualized as being formed of three major cascaded components as shown in FIG. 3. A first component is formed by convolutional layers (L1, L2, L3, L4, and L5) that can be used to suppress excessive noise in line integral data and convert a sparse view sinogram into a dense view sinogram. These layers can be used to implement a manifold learning process, to learn a noise-reduced and complete data manifold from a noise contaminated and sparse view data manifold. A second component is formed by convolutional layers (L6, L7, L8, and L9), which can be used to learn high level feature representations from the output data of the L5 layer. The third component is formed by the remaining layers (L10, L11, and L12). A fully connected layer (L10) can be used to perform a domain transform from the extracted data feature space to image space. Additionally, layers L11 and L12 can be used to learn a combination of the partial image from each view angle to generate a final image.

As described, the above implementation is just one, non-limiting example of an architecture in accordance with the present disclosure. For example, the third component, including L10-L12, could be foregone in favor of a traditional backprojection reconstruction. Thus, end-to-end training is designed to optimize the parameters of the first two components to feed into a backprojection reconstruction. As another non-limiting example, the second and third component could be replaced with a traditional filtered backprojection, in which case the end-to-end training optimizes the parameters in the first stage for reconstruction.

Irrespective of the particular architecture, parameters in all layers can be directly learned from input data 302 and training images in the training data set. The iCT-Net architecture 300 enables the reconstruction of images with, as a non-limiting example, a 512×512 matrix since the number of parameters is on the order of $Q(N^2 \times N_c)$, which is in contrast to $O(N^4)$ in other architectures. Here, N denotes the image matrix size and $N_c$ denotes the number of detector elements.

As shown in FIG. 3, iCT-Net 300 can take an acquired sinogram 302 with dimensions of $N_c \times N_v$, to generate a CT image with a matrix size of N×N (N=512), via a twelve-layer deep neural network. Here $N_v$ denotes the number of view angles.

Continuing with respect to FIG. 3, L1-L5 are five convolutional layers. L1-L3 operate along the dimension of detector elements while L4 and L5 operate along the dimension view angles. The L1 layer can have 64 convolutional kernels, each with a dimension of 3×1×1, followed by a hard shrinkage operator ($S_\lambda$) as the activation function, which is defined as:

$$S_\lambda(\text{output}) = \begin{cases} \text{output}, & |\text{output}| > \lambda \\ 0, & |\text{output}| \leq \lambda \end{cases};$$

where $\lambda$ is the threshold value. The L2 layer can present another 64 convolution kernels with a dimension of 3×1×64, followed by $S_\lambda$ as the activation. In order to learn new features from the output of the L1 and L2 layers, the original input and the feature outputs of the first two layers can be concatenated 304, 306, 308 to form inputs for the L3 layer. The L3 layer can have a single channel convolution kernel with a dimension of 3×1×129, followed by $S_\lambda$ as the activation. The hyper-parameter $\lambda$ can be empirically selected to be, as a non-limiting example, $\lambda=1\times10^{-5}$ for L1-L3 layers. In the L4 layer, there can be $\alpha_1 N_v$ convolutional kernels with the dimension of 1×1×$N_v$, followed by an activation $S_\lambda$. In the L5 layer, there can be $\alpha_2 N_v$ convolutional kernels with the dimension of 1×1×$\alpha_1 N_v$, followed by another activation $S_\lambda$. A hyperparameter value of hyper-parameter $\lambda=1\times10^{-8}$ in L4 and L5 layers and a hyperparameter value of $\alpha_1=\alpha_2=1$ can be selected for the dense view reconstruction problem, while $\alpha_1=2, \alpha_2=4$ can be used or otherwise empirically selected for the sparse view reconstruction problem with a factor of four view angle undersampling.

L6-L10 are another five convolutional layers. In the L6 layer, there is one kernel with a dimension of $N_c \times \alpha_2 N_v \times 1$ followed by a linear activation. In the L7 layer, sixteen kernels can be used with a dimension of $\beta \times 1 \times 1$, followed by a hyperbolic tangent activation (i.e., the operation of the function tanh(x)). There is one kernel with dimensions of $\beta \times 1 \times 16$ followed by a hyperbolic tangent activation in the L8 layer. There are $N_c$ kernels with dimensions of $1 \times 1 \times N_c$ followed by a hyperbolic tangent activation in the L9 layer. Finally, there are $N^2$ kernels with dimensions of $1 \times 1 \times N_c$ followed by a linear activation in the L10 layer. Hyperparameters $N=512$ and $N_c=888$ can be selected for the non-interior reconstruction problem while $N_c=222$ can be selected for the interior problem with $\varnothing=12:5$ cm FOV.

Kernels with stride one were used for all convolutional layers. All layers can be designed with bias terms except for the L6, L10, and L12 layers. Convolution operations in all convolutional layers can be performed with padding to maintain the dimensionality before and after the convolution operations.

L11-L12 layers, via devectorization 310, generate the final image 312. The dimensions of the output of the L10 layer can be $\alpha_2 N_v \times N^2$. For each of the $\alpha_2 N_v$ channels, the $N^2$ values can be reshaped into a matrix with a size of N×N. The matrix can then be rotated around its center by an increment angle $\phi=(\alpha_2 N_v - i)\Delta\phi$, $(i=1, 2, \ldots, \alpha_2 N_v)$ followed by a bilinear interpolation to make sure the rotated matrix stays on a Cartesian grid. Hyperparameter $$\Delta\phi = \frac{\pi}{492}$$

can be selected. The rotated matrix can then be reshaped back to a column vector with dimension of $N^2$. The L12 layer combines the contribution from each of the $\alpha_2 N_v$ channels via a convolution kernel with dimension $1\times1\times\alpha_2 N_v$ followed by a linear activation to generate the final image 312 with size of $N^2$. Note that the introduction of a separated rotation layer (L11) can be used to reduce the dimension of learnable parameters in L10 from $\alpha_2 N_v N_c N^2$ to $N_c N^2$ and makes L10 trainable using limited GPU memory designed for personal computers.

To help keep track the number of training parameters and the dimension of each layer, these parameters are summarized in Table 1.

|  | L1 | L2 | L3 |
|---|---|---|---|
| Parameters | 64, 3 × 1 × 1 | 64, 3 × 1 × 64 | 1, 3 × 1 × 129 |
| Output | 64, $N_c \times N_v$ | 64, $N_c \times N_v$ | 1, $N_c \times N_v$ |
|  | L4 | L5 | L6 |
| Parameters | $\alpha_1 N_v$, 1 × 1 × $N_v$ | $\alpha_2 N_v$, 1 × 1 × $\alpha_1 N_v$ | 1, $N_c \times \alpha_2 N_v \times 1$ |
| Output | $\alpha_1 N_v$, $N_c \times 1$ | $\alpha_2 N_v$, $N_c \times 1$ | 1, $N_c \times \alpha_2 N_v$ |
|  | L7 | L8 | L9 |
| Parameters | 16, $\beta \times 1 \times 1$ | 1, $\beta \times 1 \times 16$ | $N_c$, 1 × 1 × $N_c$ |
| Output | 16, $N_c \times \alpha_2 N_v$ | 1, $N_c \times \alpha_2 N_v$ | $N_c$, 1 × $\alpha_2 N_v$ |
|  | L10 | L11 | L12 |
| Parameters | $N^2$, 1 × 1 × $N_c$ | n/a | 1, 1 × 1 × $\alpha_2 N_v$ |
| Output | $N^2$, 1 × $\alpha_2 N_v$ | $\alpha_2 N_v$, $N^2 \times 1$ | 1, $N^2 \times 1$ |

Each entry in Table 1 consists of the first number to denote the number of kernels and the tuple followed the coma denotes the dimension of the used kernel in each layer. For example, (64,3×1×1) in L1 layer means that there are 64 kernels with dimensions 3×1×1.

To maximize the potential generalizability of the trained iCT-Net, training datasets can be maximally expanded to include a wide variety of human anatomy at a wide variety of x-ray exposure levels. Although it is possible to access the anonymized clinical CT image data with a variety of human anatomy and other animal anatomy, it can be very difficult to obtain data with a wide variety of radiation dose levels. Additionally, the quality of training data acquired from real CT scanners may be compromised due to physical confounding factors such as beam hardening, scatter, the x-ray tube heel effect, and the limited dynamic range of x-ray detectors. To control the impact of these confounding factors without compromising the applicability of the trained iCT-Net in experimental evaluations, a two-stage training strategy can be used.

The first training stage can be performed using numerical simulation data and the second training stage was performed using, for example, experimental data acquired from a 64-slice MDCT scanner.

Stage-1 Training can include a segment-by-segment pre-training phase followed by an end-to-end training phase. The pre-training for the segment L1-L3 can be performed using paired training data with low dose (high noise) projection data as input and high dose (low noise) projection data as output. The segment L4-L5 can be pre-trained using sinograms with sparse view angles as input and sinograms with dense view angles as output. The segment L7-L9 can be pre-trained using sinogram data with dense view angles as input and the corresponding sinograms filtered with a conventional Ram-Lak filter as output. Note that for the interior problem, the input sinogram data can be truncated, but the output data used in pre-training can be a correspondingly truncated portion of the filtered data generated by applying the Ram-Lak filter to the non-truncated data. In the segment-by-segment pre-training stage, the weights can be initialized as Glorot uniform distribution random numbers, and biases can be initialized as zeros. In one implementation, the batch size was fixed to 100 in each segment-by-segment pre-training phase and 100 epochs were used as the empirical stopping criterion. In this non-limiting example, the number of training samples for the pre-training of each segment was 3,747,072 for the L1-L3 segment, 3,381,504 for the L4-L5 segment, 3,747,072 for the L7-L9 segment, and 3,747,072 for L10.

After pre-training all segments, input sinogram data and output reconstructed images can be used to perform the end-to-end training of the iCT-Net using simulated projection data. Stage-2 Training can form this end-to-end training step using experimental phantom data and human subject data, for example, acquired from a 64-slice MDCT scanner. In one non-limiting example, projection data of an anthropomorphic abdominal phantom (CIRS, Norfolk, Va.) were acquired at different radiation dose levels and projection data from 58 human subject cases were used to perform the Stage-2 training for the Stage-1 trained iCT-Net.

The loss function can be the correspondingly defined mean squared error in all training stages. The loss function may be minimized using the standard stochastic gradient descent technique with a learning rate of $1 \times 10^{-3}$ and decay factor of $1 \times 10^{-6}$. In one non-limiting example, thirty epochs were used as an empirical stopping criterion, batch size was fixed to 3, and training samples were randomly shuffled. The change of the loss function per epoch for both training and validation was been carefully monitored to make sure there is no overfitting problem in the entire training process.

In this non-limiting example, training was performed on the platform Keras with TensorFlow backend deep learning library and a single graphic processing unit (GPU). After the iCT-Net was trained, it took 0.14 seconds (average over all tested data conditions) to reconstruct a single image slice.

A target function $f$ to generate an image vector $x \in R^{N^2}$ from an input data set vector $y \in R^M$ can be approximated as a feedforward deep neural network with a feedforward deep network architecture with multi-layer composition of a series of nonlinear mappings (i.e., $X = f(Y) \approx \hat{f}(Y) = h^{(L)} \circ h^{(L-1)} \circ \ldots \circ h^{(l)} \circ \ldots \circ h^{(1)}$, where l denotes the layer index and L denotes the total number of layers). The output from a previous layer is the input for the next layer, namely:

$$y_{c_l}^{(l)} = \zeta^{(l)}\left[\sum_{c_{l-1}=1}^{C_{l-1}} W_{c_{l-1},c_l}^{(l)} y_{c_{l-1}}^{(l-1)} + b_{c_l}^{(1)}\right],$$

where $\zeta^{(l)}$ denotes the activation function for the $l^{th}$ layer, $c_l \in \{1, 2, \ldots, C_l\}$ denotes the feature channel index in the $l^{th}$ layer, and $C_l$ denotes the total number of features in the $l^{th}$ layer. Also, $y_{c_l}^{(l)}$ denotes the $c_l^{th}$ feature in the $l^{th}$ layer, $W_{c_{l-1},c_l}^{(l)}$ denotes the $l^{th}$ layer linear mapping that transforms the $c_{l-1}^{th}$ feature at the previous layer to the $C_l^{th}$ feature at the current layer, and $b_{c_l}^{(1)}$ denotes the bias in the $l^{th}$ layer. To simplify the notation and help avoid confusion, a compact notation without subscript indices is introduced to denote the input-output relationship at the l-th layer as $Y^{(l)} = h^{(l-1)}(Y^{(l-1)})$.

Using the above notation, the output image $\hat{x} := y^{(l)} = \hat{f}(y)$ is parameterized) by a group of parameters $\{W_{c_{l-1},c_l}^{(l)}\}$ and $\{b_{c_l}^{(1)}\}$. Using the mean least square error as the goodness metric, a loss function is defined to optimize the unknown weights and bias parameters by solving the following optimization problem:

$$\{W_{c_{l-1},c_l}^{*(l)}, b_{c_l}^{*(1)}\} \arg\min \frac{1}{2N_s} \sum_i \|\hat{f}(y_i) - x_i\|_2^2,$$

where $i \in \{1, 2, \ldots, N_s\}$ denotes the index of the training sample, and $N_s$ denotes the total number of samples.

To perform the backpropagation procedure for the proposed iCT-Net framework, the gradients in each layer need to be calculated. Most of the gradient computation is similar to other well-known convolution neural network (CNN) models except that some extra care is needed for the layer with rotation operations (the L11 layer). Nevertheless, the calculations are purely algebraic. L denotes the loss function and $\Theta^{(l)}$ denotes the unknowns to be learned at the $l^{th}$ layer. The associated gradient $$\frac{\partial L}{\partial \Theta^{(l)}}$$

can be obtained through backpropagation as:

$$\frac{\partial L}{\partial \Theta^{(l)}} = \frac{\partial y^{(l+1)}}{\partial \Theta^{(l)}} \frac{\partial y^{(l+2)}}{\partial y^{(l+1)}} \cdots \frac{\partial y^{(l)}}{\partial y^{(L-1)}} \frac{\partial L}{\partial y^{(L)}}.$$

Here we need to calculate four types of gradients:

$$\frac{\partial y^{(l+1)}}{\partial W^{(l)}} = \frac{\partial h^{(l)}(y^{(l)})}{\partial W^{(l)}},$$

$$\frac{\partial y^{(l+1)}}{\partial b^{(l)}} = \frac{\partial h^{(l)}(y^{(l)})}{\partial b^{(l)}},$$

$$\frac{\partial y^{(l+2)}}{\partial y^{(l+1)}} = \frac{\partial h^{(l+1)}(y^{(l+1)})}{\partial y^{(l+1)}},$$

$$\frac{\partial L}{\partial y^{(L-2)}} = R^{-(\alpha_2 N_v - i)} \frac{\partial L}{\partial y^{(L-1)}},$$

where $i = 1, 2, \ldots, \alpha_2 N_v$.

The first three gradients were calculated using the numerical routines provided by TensorFlow. Compared to $R^{\alpha_2 N_v - i}$ which rotates the $i^{th}$ channel of the output at the L10 layer by the angle of $\phi_i = (\alpha_2 N_v - i) \Delta\phi$, in the feedforward path, its gradient, the operation $R^{\alpha_2 N_v - i}$ rotates the difference between the model output and desired output, $Y^{(L)} - X$, by the angle of $-\phi_i$ in the backpropagation path to form the gradient at the L11 layer. Image rotation and resampling were implemented using TensorFlow operations and incorporated as a layer in Keras to numerically rotate the image matrix by $\phi_i$ (in the feedforward path) or $-\phi_i$ (in the backpropagation path) and resample the image matrix using bilinear interpolations.

Non-Limiting Example using iCT-Net.

To train the proposed iCT-Net, three types are training data were prepared, including numerical simulation data, experimental phantom data, and clinical human subject data. The preparation of the training data was presented in the following subsections.

Numerical Simulation Training Data Acquisitions. Twenty clinical CT image volumes, each containing 150-250 image slices, were used to generate simulation training data by using a standard ray-driven numerical forward projection procedure in a fan-beam geometry. The parameters for the fan-beam acquisition geometry are the same as that used in the 64-slice MDCT scanner. To generate projection data at a variety of noise levels, Poisson noise was added to each simulated projection datum. The entrance mean photon number at the reference (100%) dose level was set to be $I_0=1\times10^6$ per ray. Other reduced-dose datasets were generated with entrance photon fluence of 50%; 25%; 10%; 5% of $I_0$.

To incorporate the effect of electronic noise that may be significant at low exposure levels, zero-mean Gaussian distributed random values were added into the projection data before the log-transform to generate line integral data. The added Gaussian electronic noise has a noise-equivalent-quanta of 10 photons per ray, which is consistent with the typical electronic noise level in the MDCT scanner used in this work.

Experimental Phantom Training Data Acquisitions. Despite efforts in generating training data using numerical simulations to simulate the geometry and physics of the data generation process in a physical CT scanner, there was no specific effort in simulating the tube physics, detector physics and electronics of the physical CT scanners. Therefore, it was important to acquire experimental data from physical scanners to fine tune the iCT-Net parameters such that the trained network is able to produce desired reconstruction results for a specific CT scanner. This training stage was referred to as the scanner-specific fine-tuning training process. Given the fact that majority of the training tasks were sufficiently completed using the large data set from numerical simulations, only the anthropomorphic abdominal phantom (CIRS, Norfolk, Va.) was scanned using the 64-slice MDCT scanner in our scanner-specific training process. Specifically, the anthropomorphic abdominal phantom was scanned at six mAs levels (6, 14, 28, 56, 112, and 220 mAs) with a tube potential of 120 kV using a clinical abdominal CT scan protocol. The acquired CIRS phantom data were used to perform further training of the entire iCT-Net in an end-to-end manner. Specifically, raw sinogram data were generated. The raw sinogram data were then retrospectively sorted into different groups (short-scan, super-short scan, interior tomography with both dense view and sparse view conditions) to train the corresponding iCT-Net parameters in an end-to-end training session.

Clinical Human Subject Training Data Acquisitions. With HIPAA compliance and IRB approval, similar to the generation of experimental phantom data, raw sinogram datasets of 118 human subjects scanned with a coronary CT angiography protocol were retrospectively retrieved. A routine dose CT scan was prescribed to each subject with clinical indications. Among the 118 subjects, 58 subjects were randomly selected, and their projection data corresponding to the central detector row and the FBP reconstructed images were used to train the iCT-Net during the fine-tuning phase. The remaining 60 subjects were used as part of human subject data in our generalizability test.

To test the generalizability of the trained iCT-Net for each reconstruction task, it is critically important to test the reconstruction performance for different phantoms and different data acquisition conditions from those used in training processes. Therefore, in this non-limiting example, the data sets consist of the remaining 60 exams in our available 118 coronary CT angiography cohort (58 exams were used in training stage), as well as 5 additional abdominal CT exams that have never seen by iCTNet in training stage. Additionally, an anthropomorphic head phantom was also scanned at four available tube potentials to generate data to test the generalizability of iCT-Net to data acquired at different x-ray spectral conditions.

Experimental Testing Phantom Data Acquisitions. To significantly deviate from the anatomical conditions of the abdominal phantom used in training stage, the generalizability test of iCT-Net was performed using an anthropomorphic head phantom (PH-3 ACS, Kyoto Kagaku, Kyoto, Japan). The head phantom was scanned at each of the four different available tube potentials (80, 100, 120 and 140 kV) using the same 64-slice MDCT scanner. The tube current-exposure time product for these testing data acquisitions were 500 mAs.

Human Subject Testing Data Acquisitions. Besides the remaining 60 cases out of 118 coronary CT angiography exams which have never been used in training, with HIPAA compliance and IRB approval, tests were performed using additional 5 retrospectively abdominal CT exams scanned at 120 kV and 500 mAs to demonstrate its performance generalizability.

Reconstruction accuracy is quantified using two standard metrics. Relative root mean square error (rRMSE) and structural similarity index metric (SSIM) were used. The rRMSE is defined as follows:

$$rRMSE = \frac{\|x - x_0\|_2}{\|x_0\|_2} \times 100\%,$$

where $X_0$ denotes the reference image. The SSIM is defined as $$SSIM(x, x_0) = \frac{(2\mu_x\mu_{x_0} + a_1)(2\sigma_{x,x_0} + a_2)}{(\mu_x^2 + \mu_{x_0}^2 + a_1)(\sigma_x^2 + \sigma_{x_0}^2 + a_2)}.$$

Here $\mu_x$ denotes the mean value of image x, $\sigma_x^2$ denotes the variance of x, and similar properties are defined for the reference image $x_0$. $\sigma_{x,x_0}$ denotes the covariance of x and $x_0$, where $a_1=1\times10^{-6}$ and $a_2=3\times10^{-6}$ are two constants which are used to stabilize the division with a weak denominator. The size of ROIs used to calculate SSIM is 30 mm×30 mm.

In addition to the above metrics to assess reconstruction accuracy, line profiles across images have also been used to demonstrate the reconstruction accuracy across the images.

Results of Non-Limiting Example Using ICT-Net.

Reconstruction results for short-scan acquisition mode: dense view and sparse view reconstruction.

We first demonstrate that iCT-Net can be trained to accurately reconstruct images from data acquired in a short-scan acquisition mode for both dense view angle sampling and sparse view angle sampling conditions. For comparison, reference images were generated using the standard FBP reconstruction with a Ram-Lak filter at dense view sampling condition. To benchmark the iCT-Net reconstruction performance, an iterative reconstruction technique referred to as the compressed sensing (CS) reconstruction was implemented using a total variation regularization. The corresponding reconstruction parameters were: for the dense-view reconstruction cases, $\mu=2\times10^{-5}$. For all cases, $\lambda=0.1$, s=0.2, $N_{Iter}=15$ and $N_{denoising}=100$ were used for reconstruction. These parameters were empirically optimized for the most appealing reconstruction performance of the CS results presented. Difference images were generated by subtracting the iCTNet reconstruction results from the corresponding reference image and the rRMSE was calculated using the above equation for rRMSE to assess reconstruction accuracy.

As the first test of the generalizability of iCT-Net with quantifiable reconstruction accuracy, numerical simulation data without added noise were generated from human CT images and these sinogram data were directly used as input to the trained iCT-Net to reconstruct images. The reconstructed image and the difference image showed that iCT-Net is able to accurately reconstruct images with lower overall rRMSE values and higher SSIM values when it is compared with the corresponding CS and FBP reconstructions.

To demonstrate that the trained iCT-Net is able to reconstruct images directly from experimental data, sinogram data from human subject cases were used as input to reconstruct images. iCT-Net is able to accurately reconstruct images for both the dense view and sparse view problems, achieving a higher SSIM and lower rRMSE than the corresponding FBP and CS reconstructions.

Reconstruction results for super-short-scan acquisition mode: dense view and sparse view reconstruction.

Next, iCT-Net was demonstrated to be capable of being trained to accurately reconstruct images for the super-short scan acquisition with 180 degree angular range. In this case, there are missing data in the corresponding Fourier space. Therefore, one cannot expect the conventional short-scan FBP reconstruction to be able to accurately reconstruct the image for both the dense view and sparse view problems. After the training data sets were used to train the same iCT-Net, the trained iCT-Net was able to accurately reconstruct the image content in the same upper half of the FOV as shown in the images and line profiles. Note that, according to the modern analytical reconstruction theories, it is possible to accurately reconstruct image content in half of the FOV for a view angle range of 180 degrees, provided that the view angles are not sparse. One such method (termed LCFBP) was chosen for comparison because the derivative operations have been eliminated in LCFBP, such that it does not penalize the performance of these modern super-short scan reconstruction algorithms in sparse view angle reconstruction scenario.

When view angles are sparse, iCT-Net was able to accurately reconstruct images for the sparse view reconstruction problem. In contrast, strong aliasing artifacts appeared in the LCFBP reconstruction for the sparse view super-short scan reconstruction problem.

Although the CS method may not be strictly applicable to the super-short scan reconstruction problem with dense view or sparse view sampling, out of curiosity, the CS method was blindly applied to the super-short scan input data to reconstruct images.

C. Reconstruction results for interior tomography problem: dense view and sparse view reconstruction.

The iCT-Net reconstruction performance for the interior problem without and with sparse view acquisitions was shown to be desirable. For the interior problem, mathematical proofs are available to show that a stable solution exists for an accurate reconstruction of the interior region under the condition that either the function values are known for some interior region or the function is known a priori to be piece-wise constant. However, in either case, iterative reconstruction schemes must be employed to account for these additional mathematical constraints to regularize the reconstruction. It is important to note that the available mathematical solvability proofs of the interior problem rely on the concept of analytical continuation in complex analysis, which is incompatible with the sparse view condition.

Results for dense view angle sampling and sparse view angle sampling show that the same iCT-Net implementation can be trained to accurately reconstruct image for the interior problem without the explicit use of the aforementioned solvability conditions. iCT-Net is able to accurately reconstruct images for both the dense view and even the sparse view interior problems down to a FOV of, for example, a diameter $\varnothing=12:5$ cm, a severe truncation situation.

To benchmark the performance of iCT-Net, extra efforts have been taken to help the FBP and CS reconstructions to perform better. Specifically, the values at the edges of the measured sinogram data were extrapolated to fill the truncated area on a view-by-view basis. Values at the truncated area were estimated by assuming an elliptical curve such that the extrapolated value smoothly drops to zero. Both standard FBP and CS methods were applied to the extrapolated sinogram. Notably, iCTNet was directly applied to the truncated sinogram, and no data extrapolation was performed while yielding superior results.

Generalizability of iCT-Net to other data conditions. The training of iCT-Net was performed using data from coronary angiography CT data sets. To test whether the iCTNet truly learned to reconstruct CT images under generic data conditions, the sinogram data acquired from the anthropomorphic head phantom at 80, 100, 120 and 140 kV tube potentials were directly reconstructed by the trained iCT-Net at the short scan condition. The trained iCT-Net was able to accurately reconstruct images directly from experimental data acquired at all four different tube potentials.

In addition to the reconstruction results for chest CT protocols, the trained iCT-Nets for the short-scan, super-short-scan, and interior problems were directly used to reconstruct images acquired from abdominal CT data. Results showed that iCT-Net was able to accurately reconstruct images for a variety types of anatomy for short-scan problems, super-short scan problems, and interior problems with and without sparse view sampling conditions.

Intermediate iCT-Net Outputs. To gain some intuitive understanding on how iCT-Net addresses difficult reconstruction problems, some of the intermediate output from the trained iCT-Net was studied. The vanishingly small difference between the intermediate output from the L5 layer and the corresponding reference dense view sinogram indicates that iCT-Net addresses the sparse view reconstruction problem by transforming the sparse view reconstruction problem into a dense view reconstruction problem. In other words, iCT-Net learns to complete the missing line integral data for those view angles for which no data acquisition was performed.

To further substantiate the above claim, the output of the L5 layer with a sparse view input sinogram was directly reconstructed using the conventional short-scan FBP reconstruction. The reconstruction results do indicate that the missing data were completed by the trained iCT-Net. As compared with the full iCT-Net reconstruction result, however, the direct FBP reconstruction L5 output generated a decent image but still has higher residual errors and thus lower reconstruction accuracy.

Although the short-scan problem with dense view sampling has been completely solved through human efforts, due to data redundancy in divergent beam data acquisitions and the resulting choice of redundant data weighting strategies, one may theoretically have infinitely many possible reconstruction solutions. A challenge in practice is how to choose proper reconstruct schemes that can best fit the data quality from a CT acquisition system. As a matter of fact, these different solutions may have different performances when applied to different strategies of using the acquired data. The data redundancy problem also exists in iCT-Net reconstruction strategy. Since the iCT-Net can be considered as a network representation of one of the many available solutions, the iCT-Net solution is actually adaptively chosen by the provided training data set. Namely, it is the provided training data set that helps iCT-Net pick up the suitable solution.

It is intriguing to note that a long-standing puzzle in deep learning methodology is its mechanism to select a solution among the many local minima in the loss function. It has been suggested that these existing local minima in the loss function might represent different solutions to the same problem. When the input data are ideal (e.g., no noise), then all these local minima may yield equivalent solutions to the same problem. For real data with non-idealities, such as noise and bias, the learning process seeks a local minimal solution which is consistent with the noise distribution presented in the training data set. The presented iCT-Net reconstruction results to the short-scan problem provide concrete examples to support this argument in deep learning methodology. Namely, the local minima in the iCT-Net loss function correspond to the network representations of the many available analytical solutions to the same short-scan reconstruction problem and the training process helps select a solution that best fits the training data.

For the interior problem with sparse view sampling, it remains unknown whether a stable solution even exists for the problem, yet iCT-Net manages to accurately reconstruct fully truncated sparse view data through deep learning. This success seems to imply that the interior problem with sparse view sampling might be meaningful and theoretically solvable provided that some appropriate constraint conditions can be explicitly formulated.

It is also important to emphasize that, to address the sparse view reconstruction problem, the conventional CS method explicitly incorporates the sparsity information into a nonlinear iterative reconstruction procedure to obtain a sparse solution. In contrast, iCT-Net offers an alternative strategy to address the CS reconstruction problem by transforming the problem into a dense view reconstruction problem and then a network approximation of the potential solution is learned from the training data. The presented results also indicate the following possibility for the future works. For the ordinary CT reconstruction problem without the severe transverse data truncations like what happened in interior tomography problem, it might be feasible to combine the first five layers in iCT-Net with the conventional FBP to perform end-to-end training to enable FBP to reconstruct a sparse view angle data set. This may open up a new opportunity to extend to the current work to the cone beam CT reconstruction problem.

Given the success in training iCT-Net to solve the super-short scan reconstruction problem, iCT-Net can also be trained to solve the intrinsic limited-view angle reconstruction problem (i.e. the intrinsic tomosynthesis reconstruction problem that is beyond the reach of the supershort-scan reconstruction algorithms).

It is also important to acknowledge that there have been many other intriguing applications of machine learning methods in x-ray CT. In these applications, it was demonstrated that the machine learning methods can be used to (1) learn patient cohort adaptive regularizers in iterative reconstruction; (2) to reduce noise; (3) to remove artifacts after the standard FBP reconstruction is applied to accomplish a domain transform from sinogram space to image space; (4) to learn adaptive filtering kernel and data redundancy weighting in FBP reconstruction; (5) to learn to optimize regularization strength in iterative image reconstruction methods; (6) to learn to perform projection data interpolation/correction before FBP is used for image reconstruction; or (7) to learn to perform image deconvolution after direct backprojection is used for domain transform. It is important to emphasize that the iCT-Net strategy is fundamentally different from these available deep learning methods in CT. iCT-Net learns the necessary domain transform on its own to accomplish high quality image reconstruction directly from the noise contaminated and incomplete sinogram data to image via an end-to-end training.

It is noted that potential challenge of generalizing iCT-Net for cone-beam CT may be addressed by modifying the current iCT-Net architecture. For example, instead of requiring more powerful GPUs, one alternative strategy is to replace the L10-L12 layers by the conventional backprojection operation, which was widely used in iterative CT reconstructions in the past decades. This is but one example of how the above-described system can be generalized or adapted to integrate with traditional reconstruction pipelines. Many other generalizations and a particular discussion of integration with traditional reconstruction pipelines is provided in detail below.

That is, using the systems described above or operating with data acquired from systems such as described above or other medical imaging systems, a new image reconstruction architecture can be implemented that is superior to traditional reconstruction systems and methods, such as those built around filtered back projection (FBP). In particular, refer to FIG. 4, a reconstruction architecture 400 in accordance with the present disclosure is illustrated and will be described with respect to a training framework.

Figure 4:
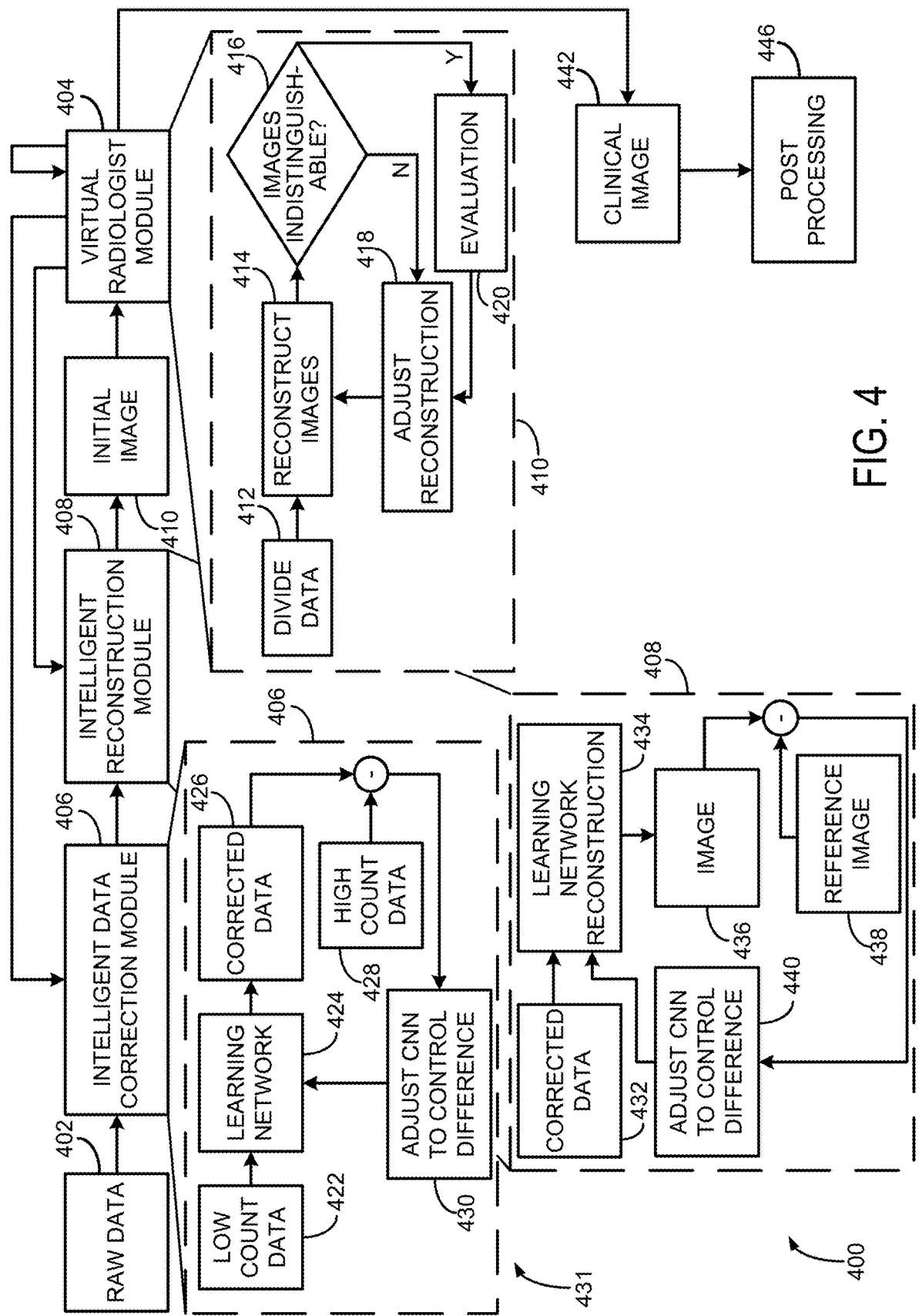
FIG. 4 is a block diagram of a general image processing and/or reconstruction architecture in accordance with the present disclosure that may be utilized with or within the systems of FIGS. 1-2C and/or other imaging systems.

Referring to FIG. 4, an architecture 400 is illustrated for taking raw data 402 processing it through a series of modules, as will be described, to be delivered to a virtual radiologist module 404 for evaluation and control of ultimate image generation. More particularly, raw data 402 is provided to an automated intelligent data correction module 406, and then an intelligent reconstruction module 408 to create an image 410. As will be described, this architecture 400 including the virtual radiologist 404, data correction module 406, and intelligent reconstruction module 408 provides a variety of advantages not available using traditional reconstruction techniques. For example, as will be described, this architecture 400 is not limited by the shortcomings and assumptions of traditional reconstruction techniques such as FBP and, thus, can readily overcome and/or separately address each category of limitation inherent in traditional reconstruction techniques, such as FBP. Also, by dividing the reconstruction architecture 400 into modules, as will be described, a given module of the reconstruction architecture 400 can be deployed into a traditional imaging system's reconstruction pipeline, without the need to replace the entire reconstruction pipeline.

In operation, the reconstruction architecture 400 receives the raw data 402 acquired by the imaging systems described above or other imaging systems for processing. First, the raw data 402, is passed to the intelligent data correction module 406, which is designed to address a second set of problems that plague CT imaging, such as problems resulting from low photon counts, as a non-limiting example.

These problems can include zero and negative CT values, problems created by taking the logarithm of a low value, and beam hardening problems. All of these and other challenges plague traditional CT processing and reconstruction.

The intelligent data correction module 406 can be focused on these low-count problems or other problems in the data that can be corrected. In the non-limiting example of low-count problems, the intelligent data correction module 406 can be passed data associated with low counts at process block 422. This low count data is then passed to a learning network at process block 424 for processing, such as will be described further hereinafter. The resulting corrected data 426 is then compared with correlated high count reference data 428. At process 430, adjustments are made to the learning network 424 to control the difference between the data during the subsequent iteration. In this way, as will be described, the learning network 424 is built that is designed to correct the low count data 422 and, thereby, control, limit, or eliminate artifacts that can be caused by zero or negative CT values, calculating logarithms of low values, or beam hardening.

The intelligent data correction module 406 can be conceptualized as forming statistical signal estimation stage 431. That is, the statistical signal estimation stage 431 handles noise and data inconsistency. Then, another module in the architecture 400 is the intelligent reconstruction module 408 that provides a robust domain transform to generate image from the corrected data. The intelligent reconstruction module 408 is designed to address a separate set of issues that can cause errors or artifacts in CT images than those described above. In particular, the intelligent reconstruction module 408 is designed to address spatial resolution issues, noise power spectrum issues (textures), and CT number accuracy issues.

Because the intelligent data correction module 406, the intelligent reconstruction module 408, and, as will be described, the virtual radiologist module 404 serve different purposes and address different inherent issues with CT images, they can be used together, as illustrated, to provide superior results compared to traditional CT reconstruction techniques. However, the virtual radiologist module 404, the intelligent data correction module 406, and the intelligent reconstruction module 408 can be used separately or selected individually to improve a traditional CT processing and reconstruction pipeline.

In the illustrated example, the intelligent reconstruction module 408 receives the corrected data from the intelligent data correction module 406; however, it may simply receive raw data 402, or differently separated data, as processed in a given processing and reconstruction pipeline, such as may be available in a commercial CT system. Regardless of the particular data used, the data is passed to a learning network designed for CT reconstruction 434. Conceptually, one may envision an FBP process as representing a shallow or very shallow learning network with hand-crafted network parameters. In this way, the FBP process can be viewed as representing a shallow or very shallow network that contains hand-crafted weight and bias parameters in the network. In contrast, the learning network 434 is a deep neural network that may include, for example, convolutional layers and fully connected layers as the backbone architecture of the deep neural network. The weighting and bias parameters in the deep learning neural network is NOT hand-crafted, instead, these parameters are learned from the pairs of training data set with pair-wise input and output data.

From the data acquired at a given projection view angle, the reconstruction produces a partial image 436. The partial images 436 from all available view angles are summed to generate the final image in a recurrent network structure. The final image is compared to a reference image 438 in the training data set. The reference image may, as a non-limiting example, be created from the high-signal/low-noise data as will be described with respect to the virtual radiologist module 404. In any case, the comparison between the image 436 and reference image 438 drives adjustments to the deep neural network to reduce or control any difference between the two at process block 440. The result, finally, is the image 410, which has been generated with the architecture 400. The image 410 may be fed into the virtual radiologist module 404 for evaluation, such as via a radiologist considering from a clinical perspective, or to serve as a reference image for a subsequent iteration of the training.

The virtual radiologist module 404 can function in a variety of roles. In one key role, the virtual radiologist module 404 is designed to address the challenge of noise that is inherent in the raw data 402 and facilitate the creation of reference data for training purposes in a deep learning network without the need for massive databases of images.

To the latter point, the virtual radiologist module 404 can facilitate the creation of a deep-learning based reconstruction process without requiring extensive repositories of reference or training data acquired from different patients and/or different imaging sessions. CT imaging systems are unlike other imaging modalities, such as ultrasound, that do not rely on ionizing radiation to acquire data and; thus, there is no inherent limitation on acquiring data like there is with CT imaging. That is, due to the ionizing radiation inherent in CT imaging, it can be difficult to create large training databases with both training and reference data.

The present disclosure overcomes this challenge using two complementary strategies. First, the raw data 402 can be divided or "shredded" at process block 412 into sub-images. For example, the raw data 402 can be segregated based on the detector element of the CT system associated with the data. In this way, the raw data 402 can be divided into individual voxels or pixels (or sub-collections of pixels, voxels, or image sections) that can be individually reconstructed. In this way, a given set of raw data 402 can provide hundreds or thousands of training opportunities for the virtual radiologist module 404, thereby greatly reducing the need to acquire a large database of data sets for training and overcoming the challenge presented by the ionizing radiation.

Second, when dividing the data at process block 412, the data can be binned based on energy level. For example, using any of a variety of techniques that will be described hereafter, the raw data 402 (irrespective of whether the data was acquired using a dual or multi-energy CT system, with an energy-discriminating detector, or a traditional energy-integrating detector) can be divided into a "low energy" or "high noise" dataset and a "high energy" or "lower noise" dataset.

Thus, process block 412 divides the raw data 402 into two data sets—one of low energy/high noise and one of high energy/lower noise—and divides the two datasets similarly into sub-collections of data—such as sub-collections of pixels, voxels, or image sections. In this way, from a single imaging session and associated dose of ionizing radiation yielding the raw data 420, a reference dataset is produced from the high energy/lower noise data, which is perfectly registered and otherwise correlated with the training dataset produced from the low energy/high noise data. Also, by similarly dividing the high energy/lower noise data and the low energy/high noise data into sub-collections of data, such as sub-collections of pixels, voxels, or image sections, a large collection of data for training is readily available from just one set of raw data 402. Thus, the present disclosure overcomes substantial limitations presented by trying to train a system based on CT imaging data.

The divided datasets (high energy/lower noise data and the low energy/high noise data divided into sub-collections) is then reconstructed at process block 414. The high energy/lower noise data may be reconstructed using a FBP reconstruction or other traditional reconstruction or may be reconstructed using the same deep-learning reconstruction that will be described below and which is used to reconstruct the low energy/high noise data. That is, of the high energy/lower noise data is reconstructed by a traditional reconstruction technique, that reconstruction technique serves as a reference. However, even if the same learning reconstruction technique is used reconstruct both the high energy/lower noise data and the low energy/high noise data, the difference between the noise levels in the datasets will initially cause an appreciable difference between the image qualities that can be used to train the reconstruction process.

That is, at decision block 416, the paired images reconstructed from the high energy/lower noise data and the low energy/high noise data for each sub-collection is compared to determine if the two paired images are indistinguishable relative to, for example, a threshold. If not, as will be the case early on during training, the reconstruction can be adjusted at process block 418 and the data can be reconstructed again at process 414, this time using the adjusted reconstruction.

Once the images are determined to be indistinguishable at decision block 416, the images may be passed for evaluation at process block 420. For example, a radiologist or collection of radiologists may review the images from a clinical perspective. In this case, the multiple images for each sub-collection may be aggregated into a traditional image of the imaging subject. Feedback from the evaluation at process block 420 may also be used to adjust the reconstruction at process block 418.

In a training context, the virtual radiologist module 404 plays the role of a human radiologist to assess image quality and provide the feedback to the intelligent data correction module and intelligent reconstruction module to fine tune the parameters such that a generated image from non-ideal data set is indistinguishable from the reference images that are generated from the almost ideal data. This module can also provide quality assessment for the non-image data. As an example, this quality assessment module can be used to assess whether the corrected data through the data correction module are indistinguishable from the ideally generated reference data. A human radiologist generally cannot provide feedback in this domain since the data are not interpretable by human. In this way, the virtual radiologist module 404 can provide feedback to the intelligent data correction module 406, the intelligent reconstruction module 408, or itself. Also, it can provide clinical images 442, which can be used clinically or subjected to further post-processing. As described above, the virtual radiologist module 404 the paired images reconstructed from the high energy/lower noise data and the low energy/high noise data. One way to achieve this ends is to spectrally separate the raw data 402.

For example, in current x-ray CT imaging, materials having different elemental compositions can be represented by nearly identical CT number. As a result, the differentiation and classification of different tissue types or contrast agents can be extremely challenging. One example of such difficulty is to differentiate between bony structures and iodinated contrast-enhanced cerebral vasculatures in CT angiography. Although these materials differ considerably in atomic number, depending on the respective mass density or iodine concentration, adjacent bone may appear identical to contrast-enhanced vasculatures. Besides, in some x-ray photon energies, the CT number of iodinated lesion is nearly as low as its surrounding normal soft-tissues. The reason for these difficulties in differentiating and quantifying different tissue types solely based on CT number is that the measured CT number of a voxel is related to its linear attenuation coefficient, which is not unique for a given material, but is a function of the material composition, the photon energies interacting with the material, and the mass density of the material.

Clinical needs of quantitative and material discriminative CT technologies have driven the development and implementation of spectral-resolved CT imaging system during past several years. Based on the widely-used energy-integrating detectors (EID), the simplest spectrally-resolved CT imaging system is a dual-energy CT (DECT), which acquires projection data at two distinct tube potentials to quantify the energy dependent attenuation coefficient at each voxel. Since interactions between material and x-ray photon are independent to the intrinsic property of the material, the energy dependent attenuation can be represented as a linear combination of two (or more) basis functions and each basis function corresponds to one dominated physical process in atomic level—Photoelectric and Compton effect or two (or more) material basis functions, like water and iodine. Spatial distributions of decomposed coefficients under these pairs of basis functions can be used for multiplication. First, to magnify the contrast level between different materials, it is desirable to reconstruct CT images as if the projection data is acquired at a much lower photon energy, in which the contribution of Photoelectric effect is more dominated than that of Compton Effect. Additionally, water (or iodine) equivalent spatial distribution could be useful since soft-tissue details and bone details of most of materials in image object could be well studied in water and iodine equivalent density images.

Besides dual-energy imaging, spectral data acquired from photon-counting detectors (PCD) and a single tube potential data acquisition offers several potential advantages. Unlike EID, which sum contributions from photons at all energies, a PCD records the number of photons received by the detector within a specific energy bin. Hence, radiation dose level in CT exam may be reduced by maximally eliminating electronic noises. Also, contrast-to-noise ratio (CNR) can be improved by optimally assigning energy bins and binning weights. The improved spectral resolution and spectral sampling provides better characterization of energy-dependent attenuation of materials, which may achieve multi-material bases decomposition and K-edge imaging.

Currently available spectral CT imaging technologies either require two different tube potential data acquisitions or leverage the spectral resolvability of PCD. Thus, both require expensive hardware. However, as will be described, the above-described architecture can be used to achieve spectral CT imaging from a single tube potential acquisition and/or using energy-integrating detectors.

In clinically available CT scanners, the x-ray source emits a polychromatic spectrum of x-ray photons. When polychromatic x-rays pass through an image object, the x-ray linear attenuation in the object depends on material composition and the photon energy. The entrance x-ray intensity after the interaction is measured by an energy-integrating detector.

The physical process can be modelled by the nonlinear integral, known as polychromatic Beer-Lamber law:

$$I(l)=I_0(l)\int_0^{E_{max}} d\varepsilon \Omega(\varepsilon)(-p(l,\varepsilon)), \qquad (1);$$

where, I(l) and $I_0$(l) are the exiting and initial photon number at l-th integral line. $E_{max}$ is the maximal energy determined by the tube potential. $\Omega(\varepsilon) \prec 0$ is a probability distribution that represents the energy distribution of entrance photon and energy response of detector. $p(l,\varepsilon)$ is the energy dependent line integral of interest, which can be represented as a line integral of the linear attenuation coefficient of image object along the l-th integral line.

Considering the following relationship between energy-integrated line integral and energy-resolving line integral:

$$y(l) := -\ln\left(\frac{I(l)}{I_0(l)}\right) = -\ln \int_0^{E_{max}} d\varepsilon \Omega(\varepsilon) \exp(-p(l,\varepsilon)); \qquad (2)$$

where, y(l) is the measured energy-integrated line integral and $p(l,\varepsilon)$ is the energy-resolving line integral.

Within this framework, the goal is to find $p(l,\varepsilon)$ to fully characterize the energy dependent property of a given image object. This is impossible with only a single measurement y(l). As described, state-of-the-art methods relying on expensive hardware have addressed this question using either two different tube potentials acquisition or energy-resolving photon-counting detectors.

In particular, using the energy-integrating detector, dual energy imaging strategy scans the same material using two different x-ray spectra with two different tube potentials: $\Omega_1(\varepsilon)$ and $\Omega_2(\varepsilon)$:

$$y_1(l) := -\ln\left(\frac{I_1(l)}{I_0(l)}\right) = -\ln \int_0^{E_{1,max}} d\varepsilon \Omega_1(\varepsilon) \exp(-p(l,\varepsilon)), \qquad (3)$$

$$y_2(l) := -\ln\left(\frac{I_2(l)}{I_0(l)}\right) = -\ln \int_0^{E_{2,max}} d\varepsilon \Omega_2(\varepsilon) \exp(-p(l,\varepsilon)).$$

As described, instead of summing up contributions of x-ray photons at all energies, the energy-resolving photon-counting detector records the number of photons received by the detector within a specific energy bin. This can be mathematically illustrated by:

$$y(l) := -\ln\left(\frac{I(l)}{I_0(l)}\right) = -\ln \int_0^{E_t} d\varepsilon \Omega(\varepsilon) \exp(-p(l,\varepsilon)), \qquad (4)$$

$$Y_2(l) := -\ln\left(\frac{I_2(l)}{I_0(l)}\right) = -\ln \int_{E_t}^{E_{max}} d\varepsilon \Omega(\varepsilon) \exp(-p(l,\varepsilon));$$

where, $E_t$ is the energy threshold value.

With two distinct measurements, $y_1$(l) and $y_2$(l), it is still insufficient to characterize $p(l,\varepsilon)$. If no additional prior knowledge is leveraged, the best that can be done is to perform a linear interpolation for each l independently. Apparently, a linearly interpolated spectral variation curve deviates from the truth as it can only represent the first order approximation of $p(l,\varepsilon)$. Even though, using photon-counting detector, more than two measurements can be generated using more than one energy thresholds, the spectral sampling density is still quite limited. If $p(l,\varepsilon)$ is represented in terms of a linear combination of two or more known energy basis functions, then, the $p(l,\varepsilon)$ can be determined once the combination coefficient onto these basis functions can be determined.

It is well known that photoelectric absorption and Compton scattering effects are two dominant x-ray photon attenuation process over the diagnostic x-ray energy range, 20 keV to 140 keV. Since interactions between material and uncharged particle like x-ray photon are independent to the property of material, the energy dependent attenuation coefficient of the image object can be decomposed as linear combination of products of spatial-dependent and energy-dependent components:

$$\mu(\vec{x},\varepsilon) = c_1(\vec{x})b_1(\varepsilon) + c_2(\vec{x})b_2(\varepsilon), \qquad (5)$$

$$c_1(\vec{x}) = \frac{\rho Z^5}{A}(\vec{x}),$$

$$c_2(\vec{x}) = \frac{\rho Z}{A}(\vec{x}),$$

$$b_1(\varepsilon) = N_A 4\sqrt{2}\, a^4 \frac{8\pi}{3} r_e^2 \varepsilon^{-\frac{7}{2}},$$

$$b_2(\varepsilon) = N_A \frac{8\pi}{3} r_e^2 f_{KN}(\varepsilon);$$

where, $c_1(\vec{x})$ is the spatial distribution of Photoelectric coefficients and $c_2(\vec{x})$ is the spatial distribution of Compton coefficients. $b_1(\varepsilon)$ is the energy-dependent Photoelectric component and $b_2(\varepsilon)$ is the energy-dependent Compton component. $\rho$, NA and A are the mass density, Avogadro's constant and atomic mass. Z is the atomic number, $\alpha$ is the fine-structure constant, $r_e$ is the classical radius of an electron, and $fKN(\varepsilon)$ is the Klein-Nishina function.

Taking the line integral operation both side for Eqn. 5, gives:

$$p(l,\varepsilon)=p_1(l)b_1(\varepsilon)+p_2(l)b_2(\varepsilon),$$

$$p(l,\varepsilon)=\int_l d\vec{x}\, \mu(\vec{x},\varepsilon),$$

$$p_1(l)=\int_l d\vec{x}\, c_1(\vec{x}),$$

$$p_2(l)=\int_l d\vec{x}\, c_2(\vec{x}). \qquad (6).$$

Two distinct measurements $y_1$(l) and $y_2$(l) can be obtained from either dual tube potentials acquisition using energy-integrating detector or single tube potential acquisition using photon-counting detector. Within known $b_1(\varepsilon)$ and $b_2(\varepsilon)$, $p_1$(l) and $p_2$(l) can be determined by a decomposition procedure for each l-th measurement independently. Energy-resolving line integral $p(l,\varepsilon)$ can then be determined according to Eq.6. $c_1(\vec{x})$ and $c_2(\vec{x})$ are directly related to spatial distribution of $\rho$, A and Z. Hence, image reconstruction procedure to determine $c_1(\vec{x})$, $c_2(\vec{x})$ and $\mu(x,\varepsilon)$ from $p_1$(l), $p_2$(l) and $p(l,\varepsilon)$ enables most of clinical applications of spectral CT imaging.

Thus, state-of-the-art strategies to achieve spectral CT imaging either require two different tube potentials data acquisition or leverage the spectral resolvability of photon-counting detector, both of which are dependent upon expensive hardware—extra or switched sources or energy-discriminating detectors. However, as briefly described above and as further detailed below the systems and methods of the present disclosure can overcome these challenges, without the specialized hardware. That is, the systems and methods achieve spectral resolvability from a single tube potential measurement and energy-integrating detector.

To further explain this implementation, it is desirable to first establish a mapping between energy-integrated and energy-resolving line integrals of an image object for each integral line independently.

The energy-resolving line integral for a specific integral line $p: \Re \mapsto \Re$ can be considered as a point at high-dimensional Euclidean space embedded onto a low-dimensional (one-dimensional) manifold $P=\{p \in \Re^{N_E} | p \in P\} N_E$ is the dimension of energy-resolving line integral at high-dimensional Euclidean space. Note that, p is described using the regular Euclidean coordinate system, namely, $(\varepsilon, p(\varepsilon))$ is a point of p. We may equivalently describe the point p using the intrinsic coordinate system of P as y, such that, there exists a pair homeomorphic and invertible mapping, $f: P \mapsto \Re$ and $f^{-1}: \Re \mapsto P$ satisfy $y=f(p)=-\ln\ (\Omega, \exp(-p))$ and $p=f^{-1}(y)$.

Hence, an identical representation $p=f^{-1}(y)=f^{-1} \circ f(p)$ can be established. Instead of determining an identical representation, the learning system of the present disclosure is able to directly learn the smooth mapping $f^{-1}$ by constructing a mapping $\hat{f}^{-1}$ that approximates $f^{-1}$ at an arbitrarily high accuracy. The mapping approximation process can be described by considering the idealized scenario where the input energy-integrated line integral and energy-resolving line integral are noiseless.

The present disclosure recognizes that there exists an unknown smooth mapping $f^{-1}$, such that $p=f^{-1}(y)$. The non-ambiguity of $f^{-1}$ functions as a surrogate of the proof of existence. The non-ambiguity of $f^{-1}$ indicates that, $f^{-1}$ is either a one-to-one correspondence (bijective) or many-to-one correspondence (surjective-only). Namely, $\forall y \in \Re$, it can only be mapped to a single point $p \in P$ by $f^{-1}$, given by the prior knowledge that $p(\varepsilon)$ is strict monotonic decreasing with respective to a $\varepsilon$.

Considering $f(p)=-\ln\ \langle \Omega, \exp(-p) \rangle$, according to integral mean value theory, $\exists \varepsilon_0 \in [0, E_{max}]$, such that, $f(p)=p(\varepsilon_0)$. Now, we assume that another point q E P, such that, $f(q)=p(\varepsilon 0)$. $q(\varepsilon)$ is also strict monotonic decreasing.

The following proof goes with three possibilities. First, $q(\varepsilon 0)=p(\varepsilon 0)$. In this case, p and q intersect at $\varepsilon 0$, the effective energy of p. $\exists \varepsilon 1=\varepsilon 0$, such that, $f(q)=q(\varepsilon 1)$. According to the condition, $f(q)=p(\varepsilon 1)=p(\varepsilon 0)$. Together with the assumption, $q(\varepsilon 0)=p(\varepsilon 0)$, we can immediately find that, $q(\varepsilon 1)=q(\varepsilon 0)$. It cannot be true since it contradicts to the prior knowledge that $q(\varepsilon)$ is strict monotonic decreasing. Second, $q(\varepsilon 1)=p(\varepsilon 1)$. In this case, p and q intersect at $\varepsilon 1 \neq \varepsilon 0$, different from the effective energy of p. Same as the previous case, $\exists \varepsilon_1 \cdot \varepsilon_0$, such that, $f(q)=q(\varepsilon 1)$. According to the condition, $f(q)=p(\varepsilon 0)$, we have $q(\varepsilon 1)=p(\varepsilon 0)$. Together with the assumption, $q(\varepsilon 1)=p(\varepsilon 1)$, we find that, $p(\varepsilon 0)=p(\varepsilon 1)$. It cannot be true since it contradicts to the prior knowledge that $p(\varepsilon)$ is strict monotonic decreasing.

Finally, $q(\varepsilon) \neq p(\varepsilon), \forall \varepsilon \in [0, E_{max}]$. In this case, there are no intersections between p and q. Considering the equation $-\ln\ \langle (\Omega, \exp(-p)) \rangle = -\ln\ \langle \Omega, \exp(-q) \rangle$, since logarithm function is monotonic, we have, $\langle \Omega, \exp(-p) - \exp(-q) \rangle = 0$. According to integral mean value theory, $\exists \varepsilon_2 \in [0, E_{max}]$, such that, $\exp(-p(\varepsilon 2))=\exp(-q(\varepsilon 2))$. Since exponential function is also monotonic, we have $p(\varepsilon 2)=q(\varepsilon 2)$. It cannot be true since it contradicts to the assumption that, $q(\varepsilon) \neq p(\varepsilon), \forall \varepsilon \in [0, E_{max}]$.

From the above, the mapping $f^{-1}$ is not ambiguous as long as it is valid that $p(\varepsilon)$ is strict monotonic decreasing. Apparently, it may not be valid for materials with k-edges at diagnostic x-ray photon energy range, such as iodine. Hence, in the later discussion and results presentation, the target is to learn $f^{-1}$ to generate accurate estimation of $p(\varepsilon), \forall \varepsilon \in [40, 140]$ keV.

A set of mappings, S, can be defined such that, $f^{-1} \in S$. That is, based on the existence of $f^{-1}$, a set of mappings can be defined, such that, $f^{-1} \in S$. The desired mapping $f^{-1}$ can be approximated as a multi-layer composition of a series of nonlinear functions $S^{(l)} \in S$ such as, $f^{-1}(y)= S^{(L)} \circ S^{(L-1)} \circ \ldots \circ S^{(1)}(y)$. $l \in \{1, 2, \ldots, L\}$ is the index of layer. From the standpoint of optimization, it is desired to maximally leverage the simplicity of linear transforms and minimally introduce nonlinear transforms to form S.

Hence, the unified representation of these transform can be represented as:

$$y_{c_l}^{(l)} = s^{(l)} \left( \sum_{c_{l-1}} W_{c_{l-1}, c_l}^{(l)} y_{c_{l-1}}^{(l-1)} + b_{c_l}^{(l)} \right); \quad (7)$$

where $s^{s^{(l)}}(\cdot)$ is the activation function for l-th layer and L is the total number of layers. $c_l \in \{1, 2, \ldots, C_l\}$ is the feature channel index in the l-th layer and $C_l$ is the total number of features in the l-th layer. $y_{c_l}^{(l)}$ is the $c_l$-th feature in the l-th layer. $W_{c_{l-1}, c_l}^{(l)}$ is the l-th linear mapping that transforms $C_l$-th feature at previous layer, l-1, to the $C_l$-th feature at the current layer, l. $W_{c_{l-1}, c_l}^{(l)}$ together with comprise the linear transform at l-th layer. To facilitate the notation, at a specific layer, all features can be concatenated to form: $y^{(l)}=\{y_1^{(l)}, y_2^{(l)}, \ldots, y_{c_l}^{(l)}, \ldots, y_{C_l}^{(l)}\}$. With the compact notation, the above transform can be further denoted as $y^{(l)}=S^{(l)}(y^{(l-1)})$.

The loss function to quantify the goodness of the estimated mapping $f$ can also be defined. $\hat{f}^{-1}$ is parametrized by a group of unknown linear transforms $\hat{f}^{-1}$ and $\{b_{c_l}^{(l)}\}$. By defining the loss function quantifying the goodness of the estimated mapping $\hat{f}^{-1}$, these unknown linear transforms can be optimized in a supervised learning scheme:

$$\underset{\{W_{c_{l-1}, c_l}^{(l)}\}, \{b_{c_l}^{(l)}\}}{\operatorname{argmin}} \frac{1}{N_s} \sum_i d\left(\hat{f}^{-1}(y_i), p_i\right); \quad (8)$$

where $i \in \{1, 2, \ldots, N_S\}$ is the index of discrete sample of P, and $N_S$ is the total number of samples. d(x,y), measuring the distance between points x and y, is a normed metric of manifold P. The point set $(y_i, p_i)$ is a pair of discrete sampling between the intrinsic coordinate space of P and P itself. $\hat{f}^{-1}(y_i)$ is the estimation of i-th sample in the intrinsic coordinate space being mapped back to P. $p_i$ produced by the underlying mapping $f^{-1}$, is the known true i-th sample embedded on P. The essential purpose of learning procedure is to pick up the best mapping, $\hat{f}^{-1}$, between the intrinsic coordinate space of P and P itself, from a set of mappings, S, by considering limited discrete samplings $(y_i, p_i)$.

Figure 8:
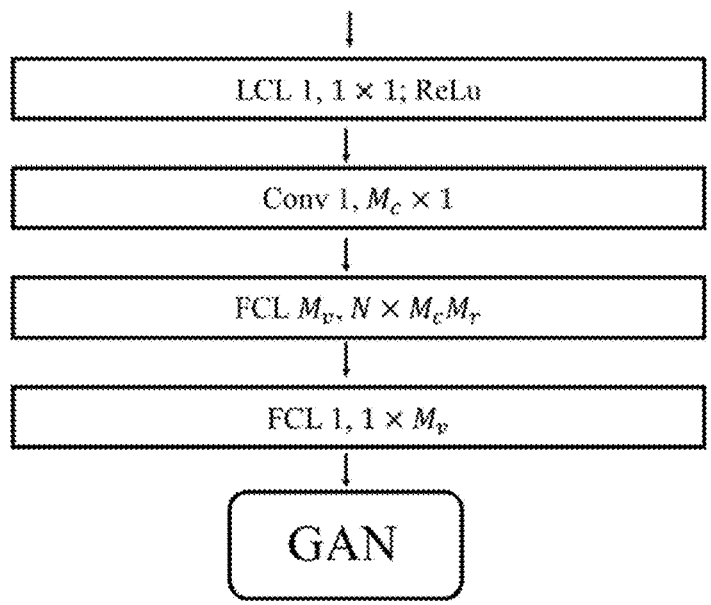
FIG. 8 is a schematic illustration for a convolutional neural network in accordance with the present disclosure.

Based on Eqn. 6, $\hat{f}^-$ can be modelled as a multi-layer neural network as shown in FIG. 8. Except for the input and output layer, all other layers are fully-connected, with $C_l$ as the number of feature channels at l-th layer. $D_{l-1}$ and $D_l$ are input and output dimensions at l-th layer. The rectified linear unit (ReLu) is used as activation function. Take the $E_{max}=140$ keV as an example, $D_1$-$D_7$=20, 40, 60, 80, 100, 120, 140, respectively.

Following similar principles as described above, to make the trained network as generalizable as possible, energy-integrated and energy-resolving projection datasets can be used, as well as diverse human anatomy. Again, however, such datasets are very difficult to obtain using experimental or clinical data acquisition systems. Besides, simulation-based training datasets may not fully represent the scanner-specific or data acquisition-related properties such as x-ray spectrum with filtrations, exact energy response of detector, scatter effects, bowtie filter, finite focal spot or other non-ideal detection situations. As such, simulation-based pre-training and experiment-based fine-tuning strategy are proposed to resolve two aforementioned concerns.

Cost function defined in Eqn. 7 can be optimized with the known stochastic gradient descent techniques such as Adam algorithms with gradient back-propagation. Learn rate ($\gamma=0.001$), $\beta1=0.9$, $\beta2=0.999$, $E=10^{-8}$ are fixed in all training processes. For the optimization of non-convex problems, initializations, stopping criterion, and training batch size are important. A Glorot uniform initializer can be used to initialize weighting matrices and bias vectors are initialized as zeros. The stopping criterion can be empirically fixed as, for example, 100 full iterations. In one implementation, the batch size used in all training processes were 100 samples.

In one non-limiting example, to facilitate the training, we designed a two-phasic pre-training procedure. In the phase 1, we only consider four most dominated materials and learn the desired mapping for each material individually. In the phase 2, more materials are considered in numerical phantoms and used to train a four-channel network, for each channel, network parameters are initialized using those learned at phase 1. Based on this design, the number of channels in the architecture, $C_1$-$C_8$=4. For the last layer, for each energy bin, four-channel outputs of previous layer are linearly combined according to contributions of each channel. Hence, the number of channels in the last layer equals to the total number of energy bins of energy-resolving data, $D_7$. The combination coefficients of the last layer is initialized by the intersection length of a given x-ray passing through each material used in phase 1. After the combination, the output dimension of last layer for each channel, $D_8$=1.

In the pre-training phase 1, we only consider four most dominated materials: water, bone, iodine, and metal. From the database at National Institute of Standards and Technology (NIST), we can find the mass attenuation coefficients, $$\frac{\mu}{\rho}(\varepsilon).$$

Since the mass attenuation coefficients for most soft-tissues are nearly equivalent to that of water, linear attenuation coefficients of soft-tissues can be approximated by water scaled by a range of densities. Hence, for each material, several mass densities are used to diverse the training datasets and simulate the case for diluted solutions or compounded mixtures: mass densities of water-equivalent soft tissues, $\rho_W \in [0.5,1.5]$, bone, $\rho_B \in [1.5,2.5]$, iodine, $\rho_I \in [0.02,0.12]$ and metal, $\rho_M \in [4,5]$ with the unit of $$\frac{g}{cm^3}.$$

Intersection length of each x-ray passing through each material, $D \in [0.001,50]$ with the unit of cm. With a 0.1 sampling interval, the total number of training samples are 2.2 million.

In pre-training phase 2, the present disclosure recognized that biological tissues are mixtures, for example, fat, muscle, soft tissue, water, air, blood, bone, gray/white matter, calcium, lung tissue, breast tissue, iodine, metallic objects, and others. The numerical dataset used in this study was constructed of a large circle disc overlapping many small circular inserts for each corresponding to one kind of material. The radius of the large background is 150 mm. Inserts of iodine, muscle, lung, bone and air were located at the outer loop. For the inner loop, iodine with different densities and sizes were simulated.

The imaging geometry mimicked the Discovery CT 750 HD (GE Healthcare, WI, USA). 984 projection views were simulated equally distributed over 360 degree as a cone beam scanning geometry with 888×64 detector elements. The image volume with size of 512×512×64 is used to generate the energy-integrated and energy-resolving datasets. Material inserts were randomly relocated and resized for different image slices. The total number of training samples in phase 2 were 56 million.

The polychromatic x-ray photon was simulated using the x-spectrum software—Spektr. Both 140 kVp and 80 kVp polychromatic spectra with soft filtration (0.1 mm Cu) were simulated. The spectrum was used to generate the polychromatic projections, the polychromatic forward model and material decomposition. Note that, only the datasets associated with 140 kVp was used to train the model. Datasets associated with 80 kVp were only used to generate dual-energy decomposition as a benchmark.

To make the numerical experiment as realistic as possible, the initial photon number for each detector elements was simulated following the attenuation principle of median body bow-tie filter and pre-patient filtration according to the physical instrument in the real scanner.

For the training datasets in fine-tuning phase, the present disclosure recognizes that dual-energy CT is an ideal scanner to generate datasets for training neural networks. As described above, existing dual energy CT methods include single-source fast kVp-switching, double-layer detection, dual-source gantry, and two pass scanning. In the diagnostic energy range, x-ray energy-dependent attenuation can be approximated as a combination of photoelectric absorption and Compton scattering. Hence, energy-resolving projection datasets can be generated from dual energy-integrated raw datasets.

Images generated at four representative energies were produced using the above-described systems and methods. Using the same display window, W/L:1400/300 HU, contrast level between iodinated contrast enhanced left ventricle and surrounding soft-tissues is increasing for decreasing energies. The contrast level variation can be quantitatively confirmed, which shows the CT number variation for different energy levels.

Dependence of noise level (noise standard deviation) changing with energies was investigated. A dependence of noise level on energies was mitigated. This favorable property of the present techniques enables the clinical use of virtual low-energy monochromatic images with substantially mitigated radiation dose penalty. Variations of CT number and noise level are quantified at ROI placed in left ventricle (iodine dominated) and at ROI placed in right ventricle (soft-tissue dominated).

Virtual monochromatic images at 60 keV and 80 keV were used to generate the water-equivalent and iodine-equivalent images via an image domain material decomposition procedure. These results showed the clinical comparability of the proposed technique.

Based on deep learning, spectral CT imaging can be achieved using a single tube potential data acquisition and energy-integrating detector. Spectral fidelity of predicted energy-resolving data of single material and mixture were quantitatively validated. Human subject studies show the clinical feasibility of the proposed paradigm shift for spectral CT by qualitatively assessing the virtual monochromatic images generated from a single energy-integrated dataset. The dependence of noise level on photon energies is mitigated. Besides, material decomposition shows the clinical utilities of the proposed technique.

Technical Underpinnings

As described above, the architecture 400 of FIG. 4 can be formed form a plurality of modules that are designed to perform data correction via the network in the intelligent data correction module 406. The modules, for example, the intelligent reconstruction module 408 can compute contribution to final image from each view angle via the domain-transformation deep neural network and combine contributions from each view angle via a recurrent neural network. Then, image quality can be evaluated via a generative adversarial network forming the virtual radiologist module 404.

To implement the above-described architecture 400, a deep-learning based cascaded neural network (CNN) architecture was developed for cone beam CT image reconstruction. The architecture can include four major stages, such as described above: (1) a data estimation and correction stage; (2) a reconstruction or domain transform stage; (3) a recurrent stage to combine image contribution (a partial image) from each view angle to generate a complete image; and (4) an image quality assessment stage to assess whether an image generated from stages (1)-(3) are indistinguishable from the image generated from the ideal reference image.

Figure 5:
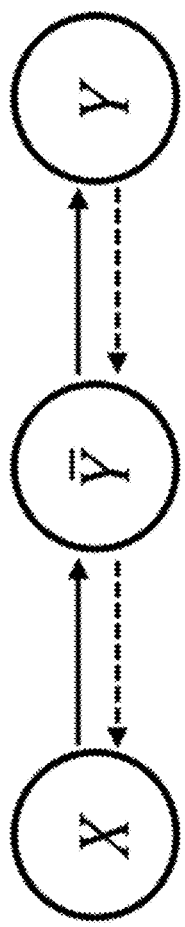
FIG. 5 is an illustration of the directed probability graph model in CT data acquisition and image reconstruction in accordance with the present disclosure.

To understand how the data correction stage works, a directed probability graph model can be used to describe the practical CT data acquisition process as a two-step process: First, data generation and, second, data corruption. For an ideal scenario ignoring noise, or any other non-idealities such as x-ray beam polychromaticity and detector non-ideality, the data generation process can be represented as a deterministic mapping by first adding x-ray linear attenuation coefficients along a path together to generate the so-called ray-sum, then taking a negative exponential, and then multiply by the entrance number of x-ray photons to generate the final number of x-ray photons detected by the ideal detector. However, in reality, the ideal data $\hat{y}$ can never be measured. Instead, a data corruption process, which can be described by the probability distribution $P(Y|\overline{Y})$, always follow the data generation process. This means that given an ideal data $\overline{y}$, the probability to draw a corrupted data y is $P(Y|\overline{Y})$. The data correction task is to estimate the ideal data $\overline{y}$ from the corrupted data, y. If one considers the image object, x, ideal data, $\overline{y}$ and measured corrupted data, y, are realizations of the following three random variables, x~P(X), $\overline{y}$~P($\overline{Y}$) and y~P(Y), their relationship can be represented as a directed probability graph model in FIG. 5. That is, FIG. 5 is an illustration of the directed probability graph model in CT data acquisition and image reconstruction. The solid arrow indicates the statistical dependence of data acquisition process and dot arrow indicates the statistical dependence of image reconstruction process.

The CT data acquisition process can be modelled for considering the joint distribution, $P(X,\overline{Y},Y)$ along the solid arrow pointing from left to right in FIG. 5. According to the statistical dependence, the joint distribution can be described as:

$$P(X,\overline{Y},Y)=P(Y|\overline{Y})P(Y|X)P(\overline{Y}|X)P(X), \qquad (9);$$

where, P (X) is the distribution of image object, $P(\overline{Y}|X)$ describes the | underlying forward model and $P(Y|\overline{Y})$ describes the underlying data corruption distribution.

The above probabilistic perspective provides foundation for both deep neural network based data correction scheme in this disclosure. It also provides a probabilistic foundation for the well-known statistical MBIR reconstruction framework. For example, the joint distribution described in Eqn. 9 can be simplified by only considering the statistical dependence between X and Y:

$$P(X,Y)=P(Y|X)P(X). \qquad (10);$$

The data distribution condition on image X can be represented as independently identical Poisson distribution over different measurements i:

$$P(Y = y \mid X = x) = \prod_i P(y_i \mid x) = \prod_i \frac{(\overline{y}_i)^{y_i} \exp(-\overline{y}_i)}{y_i!}; \qquad (11)$$

and the image prior distribution can be described as:

$$P(X=x)=Z^{-1} \exp(-\lambda\psi(Rx)), \qquad (12);$$

where, the partition function $Z=\int dx \exp(-\lambda\psi(Rx))$. The parameter $\lambda$ is used to control the relative weighting on image prior distribution. Matrix R constitutes the regularization operators as any fixed or generic basis functions (finite difference or framelets). The functional $\psi(\cdot)$ is generalized regularization functional and its definition depends on the specific knowledge of the image estimation.

The maximum a posteriori (MAP) approach aims to find the best image estimation by maximizing the logarithmic likelihood function:

$$\begin{aligned} \hat{x} &= \underset{x}{\operatorname{argmax}} \log(P(X, Y)) \\ &= \underset{x}{\operatorname{argmax}} \{\log(P(Y \mid X)) + \log(PX))\} \\ &= \underset{x}{\operatorname{argmin}} \left\{ \frac{1}{2}(Ax - y)^T (Ax - y) + \lambda \psi(Rx) \right\}; \end{aligned} \qquad (13)$$

with quadratic approximation of $\exp(\overline{y}_i)$ up to the second order around $y_i$ and ignoring irrelevant items. $(\ )^T$ is the matrix transpose operator.

In this disclosure, the aforementioned probabilistic perspective provides a foundation to correct the non-ideally acquired data. Or in other words, to estimate the ideal data from the corrupted data. In this case, one can approximate the estimation process of the ideal data from the non-ideally acquired data by a manifold learning procedure.

Both image object x and ideal data $\overline{y}$ can be considered as points at high-dimensional Euclidean space embedded onto one-dimensional manifolds $X=\{x\in\mathbb{R}^N|\in X\}$ and $\overline{Y}=\{\overline{y}\in\mathbb{R}^M|\overline{y}\in\overline{Y}\}$. Hence, there exists a pair of homeomorphic mappings, $F:X\mapsto\overline{Y}$ and $G:\overline{Y}\mapsto X$ satisfy $\overline{y}=F(x)$ and $x=G(\overline{y})$. Hence, an identical representation $x=G(\overline{y})=G\circ F(x)$ can be established.

The practical scenario considers quantum noise, electronic noise, polychromatic spectrum-induced data inconsistency, undersampling-induced data insufficiency, or any other non-idealities as a underlying data corruption distribution, $P(Y|\overline{Y})$. A practical measurement y can be considered as a realization of random variable, Y and the point set of all these realizations clusters around the ideal data, $\bar{y}$, within a measurable distance $\|y-\bar{y}\|$. $\forall y \in Y$, the point set of all realizations, $\{y\}$, constitutes a two-dimensional manifold, $Y=\{y \in \mathbb{R}^M | y \in Y, \|y-\bar{y}\| \leq d_c\}$, expanding from the one-dimensional manifold, $\bar{Y}$.

Considering the statistical dependence of data acquisition model defined in Eqn. 8, the statistical dependence of the inverse process, namely, the image reconstruction process, can be described as:

$$P(X,\bar{Y},Y)=P(X|\bar{Y})P(\bar{Y}|Y)P(Y), \quad (14);$$

where, $P(Y)$ denotes the empirical distribution of corrupted data. $P(\bar{Y}|Y)$ describes an underlying statistical signal estimation process and $P(X|\bar{Y})$ describes a underlying domain transform process. The inverse process is shown as the dot arrow pointing from right to left in FIG. 5.

According to the statistical dependence described in Eqn. 14, as an analogy to the aforementioned mapping $G: \bar{Y} \mapsto X$, the mapping between Y and X can be described as a composition of two individual mappings, $G_2 \circ G_1$, such that, $G_1: Y \mapsto \bar{Y}$ and $G_2: \bar{Y} \mapsto X$. The target of the manifold learning is to learn optimal mappings $G_1$ and $G_2$, such that, the model distribution:

$$Q(X,\bar{X},X)=Q(X|\bar{Y}; G_2)Q(\bar{Y}|Y; G_1)P(Y), \quad (15);$$

can be established to approximate the underlying inverse distribution, $P(X,\bar{Y},Y)$. Here, $Q(\bar{Y}|Y; G_1)$ is the model distribution for statistical signal estimation determined by the mapping, $G_1$ and $Q(X|\bar{Y}; G_2)$ is the model distribution for domain transform defined by the mapping, $G_2$.

When looking to implement the manifold learning by generative adversarial network (GAN), conventionally, optimal mappings $G_1$ and $G_2$ can be learned by minimizing the Kullback-Leiber divergence (KLD) between the underlying joint distribution, $P(X,\bar{Y},Y)$ and model joint distribution, $Q(X,\bar{Y},Y)$: $KLD\{P(X,\bar{Y},Y)|Q(X,\bar{Y},Y)\}$. As KLD converges to 0, $Q(\bar{Y}|Y; G_1)$ converges to $P(\bar{Y}|Y)$ and $Q(X|\bar{Y}; G_2)$ converges to $P(X|\bar{Y})$, both the statistical signal estimation mapping, $G_1$, and the domain transform mapping, $G_2$, can be learned. Instead of directly handling joint distributions, in this non-limiting example implementation, however, these two distributions $P(\bar{Y}|Y)$ and $P(X|\bar{Y})$ can be approximated one after another using a cascaded network architecture, as will be described.

$G_1$ and $G_2$ can be learned, such that the corresponding model distribution can converge to the desired underlying distribution by constructing a feed-forward network architecture by convolutional connections or fully connections between layers. In feed-forward network architectures, the loss function should be explicitly defined as a low-level goal, for example, either to measure the similarity between pairs of model output and training label (such as mean squared error (MSE) over different samples), or to measure the similarity of model and underlying distributions (such as KLD). Such definitions of similarity is generic and are not able to consider the spatial structure or characteristics represented by pairs of model output and training label. In imaging tasks, Euclidean distance based metrics, such as MSE, are often not desirable to characterize the similarity of pairs of images since it may fail to characterize detailed structures.

Instead of making the network to achieve some low-level goals, a high-level and more abstract goals can be defined, such as, to make the model distribution indistinguishable from the underlying distribution, and then, make the network automatically learn a loss function appropriate for satisfying this goal.

Regarding the intelligent image reconstruction module 408, the present disclosure reconsiders image reconstruction and breaks from the paradigm of filtered backprojection. As described above, the above described CT imaging pipeline is based on the well-known FBP reconstruction method and thereby accommodates integration within traditional CT imaging pipelines. FBP can be represented by $f(x,y)=\int_0^\pi d\theta\, \bar{p}_f(x \cos \theta + y \sin \theta, \theta)$, where $$\bar{p}_f(\rho, \theta) = \frac{1}{\rho^2} * \bar{p}(\rho, \theta)$$

is the ideal sinogram, $\bar{p}(\rho,\theta)$, after the convolution with a kernel, $$\frac{1}{\rho^2}.$$

For a finite total number of view angles, V, the above integral can be practically approximated by $$f(x, y) = \Delta\theta \sum_v \bar{p}_f(x\cos v\Delta\theta + y\sin v\Delta\theta, v\Delta\theta),$$

$$\text{where } \Delta\theta = \frac{\pi}{V}$$

is a small incremental angle. $v \in \{1, 2, \ldots, V\}$ is the digitized view angle index. The single-view backprojection operation between two adjacent view angles, $v\Delta\theta$ and $(v-1)\Delta\theta$, can be related as the coordinator transform:

$$\bar{p}\begin{bmatrix} x\cos(v-1)\Delta\theta + \\ y\sin(v-1)\Delta\theta, (v-1)\Delta\theta \end{bmatrix} = \bar{p}_f\begin{bmatrix} (x\cos\Delta\theta - y\sin\Delta\theta)\cos v\Delta\theta + \\ (x\sin\Delta\theta + y\cos\Delta\theta)\sin v\Delta\theta, (v-1)\Delta\theta \end{bmatrix}$$

$$:= \bar{p}_f[x_r\cos v\theta + y_r\sin v\Delta\theta, (v-1)\Delta\theta]$$

$$:= R_f(\bar{p}_f[x\cos v\Delta + y\sin v\Delta\theta, (v-1)\Delta\theta]).$$

The defined mapping, $\mathcal{R}$, rotates the function $\bar{p}_f(x,y)$ with $\Delta\theta$. Using the rotation mapping, the integral approximated by summation above can be further represented as $$f(x, y) = \Delta\theta \sum_v R^{V-v}(\bar{p}_f(x\cos V\Delta\theta + y\sin V\Delta\theta, v\Delta\theta)).$$

The FBP algorithm can be implemented as two steps according to the above equation. First, projection data acquired at any view angle, $v\Delta\theta$, $V \in \{1, 2, \ldots, V\}$, is always backprojected along one specific view angle, $V\Delta\theta$. Here, the last view angle index, V, is used as an example. After the single-view backprojection, the backprojected image is rotated by repeatedly applying the rotation mapping $\mathcal{R}$ several times. Then, the reconstruction image can be obtained by summing all these backprojected-and-rotated images together. Based on such strategy, the single-view backprojection mapping can be defined to backproject data acquired at any view angle along the last view angle $$f(x, y) = \Delta\theta \sum_{v} R^{V-v}(B(\overline{p}_f(\rho, v\Delta\theta))).$$

The relation between ideal projection data and filtered ideal projection data can be represented by a domain transform mapping, $\mathscr{F}$. Hence, the above equation can be further represented as $$f(x, y) = \Delta\theta \sum_{v} R^{V-v}(B(F(\overline{p}(\rho, v\Delta\theta)))).$$

In reality, due to noise and other non-idealities in the image object and/or data acquisition system, the measured projection data deviate from the ideal.

As will be further described, in the architecture described above, one or more modules or stages can be used to address noise and other non-idealities. In one example, a pre-processing mapping $\mathcal{D}$ can be performed. With this pre-processing mapping $\mathcal{D}$, the above equation can be further represented as $$f(x, y) = \Delta\theta \sum_{v} R^{V-v}(B(F(D(p(\rho, v\Delta\theta))))).$$

The digitized representation of the above equation along spatial dimension is $$f(i\Delta x, j\Delta y) = \Delta\theta \sum_{v} R^{V-v}(B(F(D(p(k\Delta\rho, v\Delta\theta))))).,$$

where $\Delta\rho = \Delta x \cos V \Delta\theta + \Delta y \sin V \Delta\theta$ and the index k is the lexicographical order depending on spatial indices i, j.

With this established, above-described CT architecture or pipeline 400 can be summarized as the relation between the image to be reconstructed and the measured projection data at v-th view angle:

$$\vec{f} = \sum_{v} R^{V-v}\left(B\left(F\left(D\left(\vec{p}_v\right)\right)\right)\right), \tag{16}$$

where image vector $\vec{f} \in \mathfrak{R}^{N \times 1}$ is the vectorized digitized representation of $f(i\Delta x, j\Delta y)$ with lexicographical order, $\vec{p} \in \mathfrak{R}^{M \times 1}$ is the vectorized digitized representation of $p(k\Delta x, v\Delta\theta))$ at given view angle index v, $M = M_c M_r V$ is the total number of measurements, and $M_c$ and $M_r$ are the number of detector columns and rows respectively.

Although this equation is derived for two-dimensional (2D) parallel-beam geometry, all geometry-related information, hidden inside the learned backprojection mapping $\mathscr{B}_r$, is directly determined by the network design, and especially, how training datasets were generated or acquired. $\mathcal{D}$ parallel-beam geometry is used only for facilitating the introduction of the rotation mapping, $\mathscr{R}$.

Figure 6:
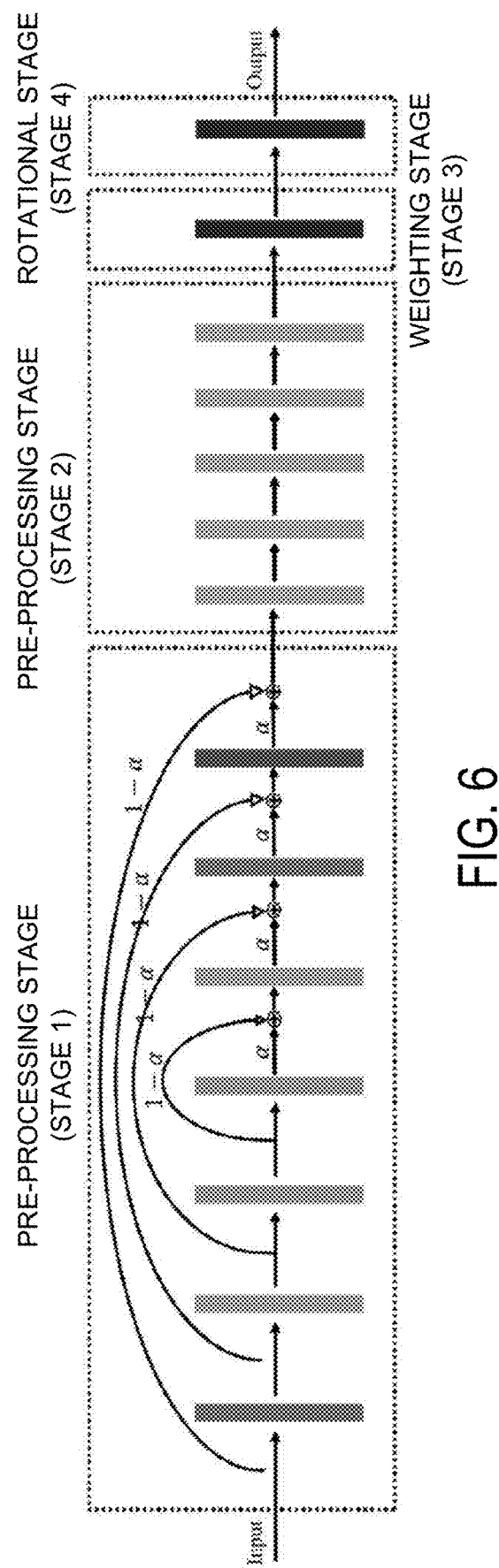
FIG. 6 is a block diagram of a model architecture for the statistical signal estimation stage of FIG. 4.

Based on the proposed model in Eqn. 16, a network was designed to include multiple individual stages. Thus, a neural network architecture in accordance with the present disclosure can be conceptually illustrated as shown in FIG. 6. In this non-limiting example, the entire network is designed to include four individual stages: (1) a manifold learning stage to perform projection data pre-processing, (2) a convolutional neural network (CNN) stage to perform data domain transform, (3) a fully connected layer with sparse regularization to perform single-view backprojection, (4) and a final fully-connected layer with linear activation to generate the target image volume. In the manifold learning stage, a combining technique was used to improve noise properties of the final reconstructed images. To make sure that each stage achieves a self-contained function, the training of the entire network can be performed in a stage-by-stage manner. Namely, training datasets and network architectures can be specifically designed for each individual stage.

A unified representation between the input and output of any layer inside any stage can be given by:

$$\vec{x}_{c_l}^{(l)} = s^{(l)}\left(\sum_{c_{l-1}} W_{c_{l-1}, c_l}^{(l)} \vec{x}_{c_{l-1}}^{(l-1)} + \vec{b}_{c_l}^{(l)}\right); \tag{17}$$

where $s^{(l)}(\cdot)$ the activation is function for l-th layer and $l \in \{1, 2, \ldots, L_1, L_1+1, \ldots, L_1+L_2, L_1+L_2+1, \ldots, L_1+L_2+L_3, L_1+L_2+L_3+1, \ldots, L_1+L_2+L_3+L_4\}$ is the index of layer. $L_1$ to $L_4$ are the total number of layers in the stage 1 to 4 respectively. $c_l \in \{1, 2, \ldots, C_l\}$ is the feature index in the l-th layer and $C_l$ is the total number of features in the l-th layer. $\vec{x}_{c_l}^{(l)}$ is the $c_l$-th feature in the l-th layer. $\vec{b}_{c_l}^{(l)}$ is the $c_l$-th bias vector in the l-th layer. $W_{c_{l-1}, c_l}^{(l)}$ is the l-th layer weighting matrix that maps $c_{l-1}$-th feature at previous layer, l–1, to the $c_l$-th feature at the current layer, l. To facilitate the notation, at a specific layer, all feature vectors can be concatenated to form a feature matrix, $X^{(l)} = \{\vec{x}_1^{(l)}, \vec{x}_2^{(l)}, \ldots, \vec{x}_{c_l}^{(l)}, \ldots, \vec{x}_{C_l}^{(l)}\}$. With the compact notation, the mapping defined in Eq.10 can be further represented as:

$$X^{(l)} = S^{(l)}(X^{(l-1)}), \tag{18};$$

where $s^{(l)}(\cdot)$ is the unified mapping for the l-th layer.

In the illustrated, non-limiting example, stage 1 is formed as a pre-processing or manifold learning stage to perform projection data pre-processing to find the mapping $\mathcal{D}$. In one non-limiting example, the first stage can be designed to learn the projection data pre-processing mapping based on the multi-layers convolutional autoencoder (CAE), because convolutional layers have been successfully applied to detect image features and sparsify image content in many tasks. However, in conventional CAE, image details may be lost in early convolutional layers, and they are challenging to recover in later layers. This difficulty may be more severe when the network goes deeper and deeper. The intrinsic noise-spatial resolution tradeoff, partially dependent on the total number of layers and the size of convolutional kernels, provided by conventional CAE may not be optimal for CT projection data correction stage. Hence, this disclosure presents a new step to provide better spatial resolution and noise properties.

To this end, unlike conventional convolution neural network models, a feature combining strategy can be used to combine features learning from early layers together with features from late layers to form the input of later layers. Mathematically, this can be represented as:

$$X^{(l)} = \begin{cases} S^{(l)}(X^{(l-1)}), & l \leq L_1/2 \\ \alpha S^{(l)}(X^{(l-1)}) + (1-\alpha)X^{(L_1-l)}, & l > L_1 2 \end{cases} ; \quad (19)$$

where α is a hyperparameter to control how much information is borrowed from early layers to form the input for later layers. For example, for simplicity, α may be fixed at 0.5. However, it does not have to be this fixed value, one may choose a different value depending upon the specific application. As described above with respect to FIG. 4, in stage 1, projection data acquired (or simulated) at a low dose level is used as the training input and at a high dose level is used as the desired output.

Figure 7:
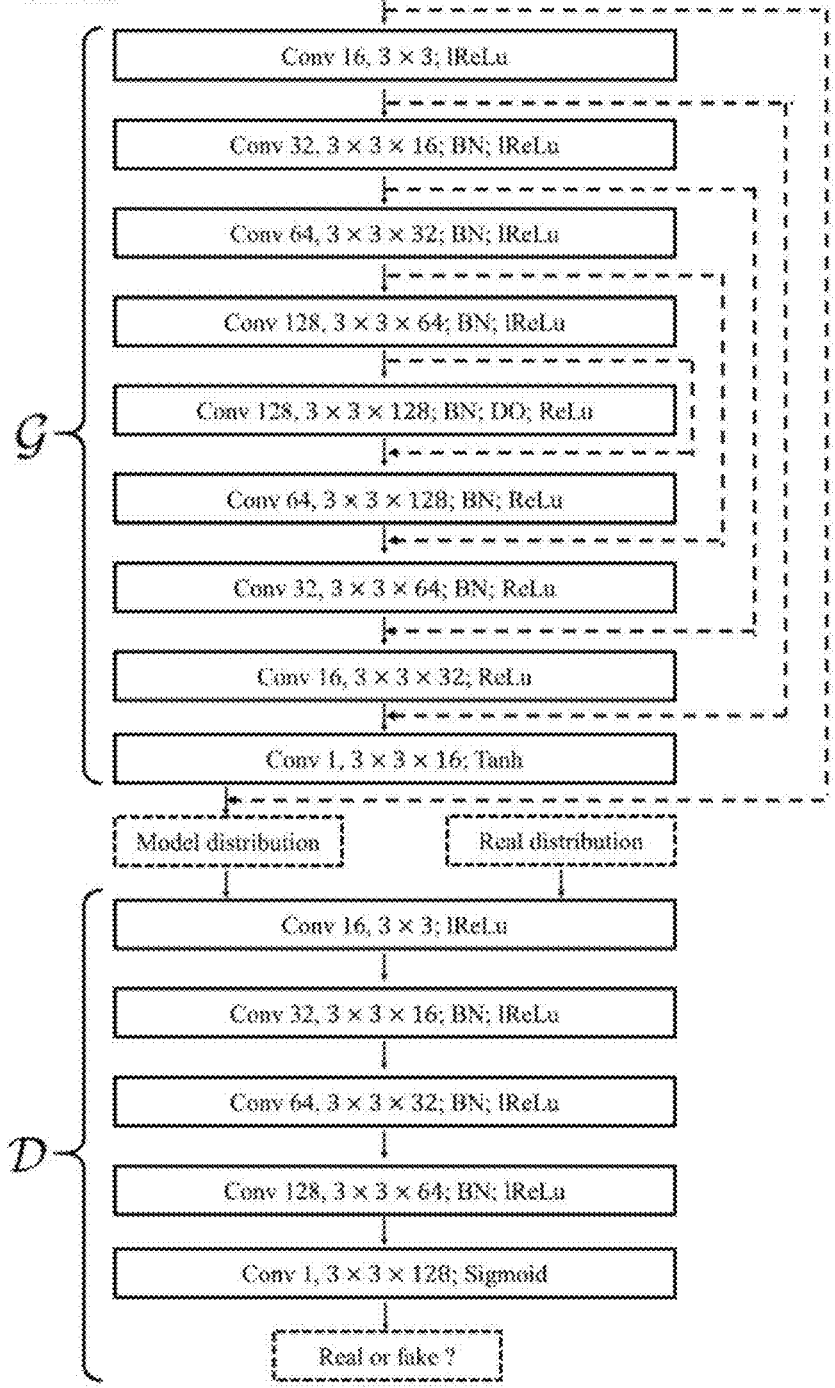
FIG. 7 is a block diagram of a model architecture of the domain transform or reconstruction stage of FIG. 4.

In the illustrated, non-limiting example of FIG. 6, stage 2 is a domain transform stage that can include a convolutional neural network designed to learn the projection data domain transform mapping $\mathscr{F}$. In stage 2, projection data without domain transform is used as the training input and with domain transform is used as the desired output. A model architecture for the statistical signal estimation described above is shown in FIG. 7. In the non-limiting example, a convolutional layer ("Cony") with kernel size of 3×3 was used as an initial default. Considering the second convolutional layer as an example, for this layer, the input feature channels is 16 and output feature channels is 32. Other acronyms are listed here: BN for batch normalization; 1ReLu for leaky rectified linear unit with 0.2 as leaky slop; ReLu for rectified linear unit; DO for dropout with a 50% dropout rate; Tanh for hyperbolic tangent function. Nine Cony layers comprise the generator and five Cony layers comprise the discriminator. Dot arrow lines describe the feature-combining connections.

The input of the stage is formed by samples drawn from Poisson noise distribution, $P(Y_0)$, and detector-received raw counts using polychromatic x-ray spectrum drawn from $P(Y)$. Sample pairs of model distribution from the generator and real underlying distribution, $P(\bar{Y}|Y)$, are inputs for the discriminator. Note that, samples drawn from $P(\bar{Y}|Y)$ are simulated as standard dose CT exams using monochromatic x-ray spectrum, $\Omega(\varepsilon) = \delta(\varepsilon - \varepsilon_0)$. The output of discriminator is a probability. By optimizing the value function defined in Eqn. 22 below, gradients can be backpropagated to update parameters in the generator.

Stage 2 can be conceptualized including a locally-connected layer (LCL). The LCL designed in stage 2 implements the logarithmic transform of detector-received counts. The logarithmic function is a nonlinear function, however, it can be approximated by a line equation within an infinitesimally local region. For each point in the signal domain, the set of line equations can be described as a linear transform, $W_{x+b}$, where the slope of each line comprises a diagonal element in matrix W and the interception comprises a element in vector b. Hence, a LCL with 1×1 kernel size followed by a ReLu function can be used to learn the desired logarithmic transform. Note that, the total number of unknowns of the LCL with 1×1 kernel size is the same as input vector dimension, in our case, $M_c$.

Continuing with respect to FIG. 6, in the illustrated, non-limiting example, stage 3 is a weighting stage configured to learn the single-view backprojection mapping $\mathscr{B}$. That is, the network in stage 3 is designed to learn the contribution (weighting) from measurements within the v-th view angle index for any image voxels. This weighting stage may include a fully-connected layer with a sparsity regularizer. Without further prior knowledge incorporated into this procedure, the mapping between image volume and projection data at v-th view angle index have to be modeled as a fully-connected layer (FCL). However, for a given image voxel, not too many measurements make significant contributions and, thus, a $l_1$ norm based regularization term can be used to promote the "sparsity" of the backprojection mapping. Considering the computational space limits, a single FLC can be used without bias vectors. To allow possible non-positive values in single-view backprojected image volume, linear activation function can be applied. In stage 3, projection data after domain transform can be used as the training input and backprojected image volume along V-th view angle index is used as the desired output.

In the illustrated, non-limiting example, stage 4 is a rotational mapping stage configured to learn the rotational mapping $\mathscr{R}$ and, thereby, generate the final image volume. In the illustrated example, the network in stage 4 is another FCL to combine contribution from all view angles into a target image volume with a linear activation function. The network in stage 4 can be designed to learn the mapping that rotates the image volume with a small incremental angle, Δθ, along with the rotation axis of the CT scanner. Since such mapping can be parametrized by a single known angle, it is essentially a coordinator transform and interpolation procedure and can be learned with a single FCL. Considering the computational space limits, a single FLC can be used without bias vectors. To allow possible non-positive values in single-view backprojected image volume, linear activation function is applied. In stage 4, backprojected image volume along V-th view angle index can be used as the training input and backprojected image volume along (V−1)-th view angle index is used as the desired output.

Figure 9:
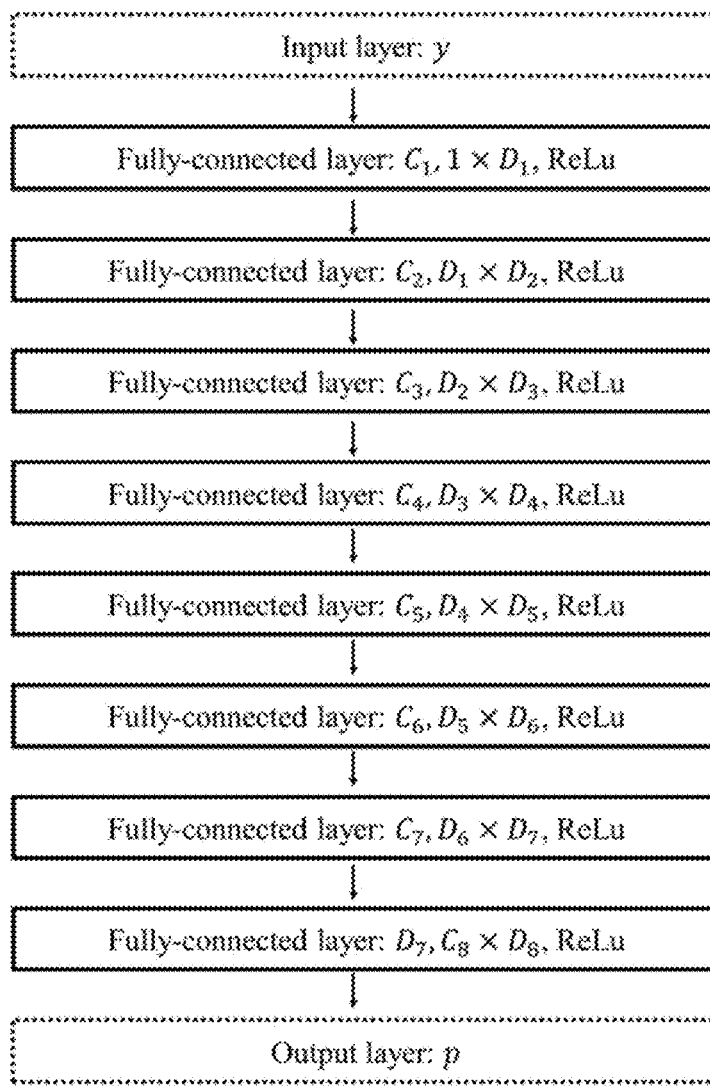
FIG. 9 is a schematic illustration for a convolutional neural network in accordance with the present disclosure for creating spectral images in accordance with the present disclosure.

A model architecture of the domain transform or reconstruction stage is illustrated in FIGS. 8 and 9. Acronyms are listed here: LCL for locally-connected layer; FCL for fully-connected layer. In this non-limiting example, designs of the first 4 layers in the stage 2 akin to the FBP algorithm of traditional CT image reconstruction, which advantageously aligns the architecture for deployment, even in modules, into existing CT pipelines. More particularly, the model may include a logarithmic transform by a locally-connected layer (LCL). In this case, instead of assuming invariance and equivariance of translation in target signal, a LCL does not share learning parameters across the entire signal support. Unlike Cony layers, a LCL can learn a set of translational-variant inner-product kernels, which extracts signal features in a translational-variant scheme. Unlike fully-connected layer (FCL), where each output neuron depends on all input neurons, correlation range in a LCL is controlled by the size of inner-product kernel, which can be designed according to the prior knowledge of the desired mapping. Hence, a LCL provides an appropriate balance between the prior assumption of desired mapping and the number of unknowns need to be learned comparing with Cony layers and FCL.

The mappings $\mathcal{D}$, $\mathcal{F}$, $\mathcal{B}$, $\mathcal{R}$ can be learned by optimizing a shared optimization function. For example, the mappings can be learned by optimizing the following problem individually for each stage:

$$\operatorname*{argmin}_{\{W_{c_{l-1},c_l}^{(l)}, \vec{b}_{c_l}^{(l)}\}} \frac{1}{N_{L_S}} \sum_i \|X_i^{(L_S)} - T_i^{(S)}\|_2^2, ; \quad (20)$$

$$l \in \{1, 2, ..., L_S\}, S \in \{1, 2, 3, 4\},$$

where $i \in \{1, 2, \ldots, N_{L^S}\}$ is the index of training sample at a given training batch. $N_{L_S}$ is the total number of training samples at a given batch in stage S. $X_i^{(L_S)}$ is the output of i-th training input at stage S. $T_i^{(S)}$ is the i-th training label (desired output). The cost function defined in Eqn. 21 can be optimized for each stage individually with a stochastic gradient descent technique. Learning rate ($\gamma$=0.001), $\beta_3 1$=0.9, $\beta 2$=0.999, $E$=10$^{-8}$ can be fixed for all stages.

TABLE 2

Parameter selections in a non-limiting example of a cascaded network architecture TRAINING

| | Stage 1 | Stage 2 | Stage 3 | Stage 4 |
|---|---|---|---|---|
| Connection topology | convolutional layers with feature combining | convolutional layers | fully-connected layer | fully-connected layer |
| Total number of layers | $L_1$ = 7 | $L_2$ = 5 | $L_3$ = 1 | $L_4$ = 1 |
| Filter kernel size | 3 × 3 | ($M_c/L_2$ + 1) × 1 | n/a | n/a |
| strides | 1 × 1 | 1 | n/a | n/a |
| Total number of features for each layer | {16, 8, 4, 4.8, 16, 1} | {1, 1, 1, 1, 1} | n/a | n/a |
| Activation function | relu | relu | linear | linear |
| Regularization | none | none | $l_1$ norm | none |
| Bias vector | with | with | without | without |
| Feature combining strength ($\alpha$) | 0.5 | n/a | n/a | n/a |

For backprojection by a multi-channel fully FCL, traditional CT image reconstruction can serve as a training starting point. In CT image reconstruction, the relationship between image and projection data, system matrix A, can be modelled as a FCL. Even if considering the fan-beam data acquisition with a single-row detector, the number of unknowns in this layer is tremendously large, not to mention the cone-beam data acquisition case. The total number of unknowns is $N_x N_y N_z \times M_c M_r M_v$ for conebeam case and $N_x N_y \times M_c M_v$ for fan-beam case. If single precision storage is used, the computational space requirement for this layer is about 1000 Gigabytes, which is unreasonably large to be held in any graphic processing units (GPU) cards designed for the above-described workstations. Besides the computational space requirement, the large number of unknowns make the training extremely difficult to avoid over-fitting.

To achieve the purpose, a multi-channel FCL can be used, where the number of channels is the number of view angles, $M_v$. Instead of considering the domain transform for all view angles at once, each channel of the layer only implement the backprojection operation for a single view angle. Even if, the total number of unknowns remains the same, however, the beauty of such multi-channel design is that, these channels can be trained individually, not simultaneously. Hence, the actual number of unknowns trained per time is reduced by a factor of $M_v \approx 1000$ in diagnostic CT. Now, the size of layer is about 1 Gigabytes for fan-beam case and 64 Gigabytes for 64-rows detector scanner, which is a much more reasonable size and can be held in multi-GPU cards.

For a given image voxel, where not too many measurements make contributions, an $l_1$-norm based regularization term can be used to promote the sparsity of the backprojection mapping. To allow possible non-positive values in single view backprojected image volume, linear activation function can be applied.

For image volume summation by a FCL, the output of the multi-channel FCL is $M_v$ image volumes. Each image volume is the backprojected image volume of a single view angle. The final image volume is the summation of all these sub-image volumes. The summation can be achieved by a FCL for each image voxel and with one as weights. The layer is designed as frozen layer, which means that, parameters of this layer is fixed and non-trainable.

The input of the stage is samples drawn from $Q(\overline{Y}|Y; G_1^*)$. The mode distribution from the generator and real underlying distribution, $P(X|Y)$, are inputs for the discriminator. The output of discriminator is a probability.

A variety of training strategies may be utilized. For example, a pre-training phase may be used for the GAN in the statistical signal estimation stage. Random Poisson distributed noise and projection datasets simulated at low dose level from polychromatic x-ray spectrum can be inputs of the generator. In this way, low-signal/high-noise data is provided. Model outputs and projection datasets simulated at standard dose level from monochromatic x-ray spectrum can be inputs of the discriminator. Glorot uniform distribution can be used to initialize weights and zeros can be used to initialize biases. Fifty full epoch was used as empirical stopping criterion. Batch size is fixed as 500. There were 86K samples for training the GAN. Learned parameters were used as initialization in a fine-tuning phase.

Pre-training can also be used for the LCL to perform logarithmic transform. Pre-log datasets and post-log datasets can be inputs and outputs for training the logarithmic transform layer. Negative ones can be used to initialize weights and ones can be used to initialize biases. Fifty full epoch was used as empirical stopping criterion. Batch size is fixed as 500. There were 55K samples. Learned parameters are used as initialization in fine-tuning phase. This layer can be considered as a frozen layer and non-trainable in fine-tuning phase.

Pre-training can also be used for the Cony layer to perform projection domain transform. Projection data before and after a known ramp kernel can be used as inputs and outputs for training the projection domain transform layer. Glorot uniform distribution can be used to initialize weights and zeros can be used to initialize biases. Fifty full epoch was used as empirical stopping criterion. Batch size was fixed as 500. There were 55K samples. Learned parameters were used as initialization in fine-tuning phase. This layer can be considered as a frozen layer and non-trainable in fine-tuning phase.

Pre-training can also be used for the multi-channel FCL to perform backprojection. Each channel of the multi-channel FCL performs the backprojection operator for a single view angle. Filtered projection data and backprojected image volume at one specific view angle can be used as inputs and outputs. Zeros can be used to initialize weights. There are no biases in this layer. Fifty full epoch was used as empirical stopping criterion. Batch size was fixed as 500. There were 5K samples. Learned parameters for a single view angle backprojection were considered as a channel of the FCL and all these channels were concatenated as the final FCL. Learned parameters were used as initialization in fine-tuning phase. This layer can be considered as a frozen layer and non-trainable in fine-tuning phase. The design of this layer only depends on the number of projections per rotation. In training each channel, a reference starting view angle, $\theta_0=0$ was assumed. For any datasets acquired from any starting view angle, $\theta$, different from the assumed $\theta_0$, the final image volume, after summing up all sub-image volumes, has to be rotated by $\theta-\theta_0$ only once.

A virtual radiologist can be implemented using the generative adversarial network (GAN). The purpose of the virtual radiologist state is to train a neural network to accomplish the following objectives: Any image or a patch of image is send into the trained virtual radiologist together with the corresponding ideally generated image or its patch, if the virtual radiologist is able to distinguish the image from the ideal counterpart, then the test image samples are not generated good enough and thus the parameters in both/or data correction stage and intelligent reconstruction stage must be adjusted to generate better image and corresponding patches. Until the trained virtual radiologist is not able to distinguish the generated image from the reference training image, then the final intelligent CT image generation pipeline training is completed.

The GAN used in virtual radiologist can be trained by training two networks simultaneously in an adversarial manner. The generator, $\mathcal{G}$, aims to generate a sample from model distribution (fake sample) to be as realistic as the sample drawn from the real underlying distribution (real sample) as possible. The discriminator, $\mathcal{D}$, aims to discriminate whether a given sample coming from the real distribution or the generated model distribution. During the training process of a GAN, $\mathcal{G}$ is optimizing to maximally deceive $\mathcal{D}$, to cause it to interpret samples from the generated distribution as real samples. At the same time, $\mathcal{D}$ is optimizing to maximally discriminate real samples from fake samples. GANs were designed to be unbiased, namely, with an appropriate model design and infinitely large training dataset, the Nash equilibrium for a GAN game is achieved, such that, $\mathcal{D}$ cannot discriminate samples from real or generated distribution, and simultaneously, $\mathcal{G}$ generates model distribution exactly recovering the underlying distribution.

To approximate the underlying statistical signal estimation process, the optimal mappings, $\mathcal{G}_1$ and $\mathcal{D}_1$, can be learned by optimizing the following cost function:

$$\min_{G_1} \max_{D_1} V(G_1, D_1) = E_{\bar{y} \sim P(\bar{Y})}[D_1^2(\bar{y} \mid y)] + E_{y \sim P(Y)}[(1 - D_1(G_1(y)))^2] \quad (21)$$

where, $V(\mathcal{G}_1, \mathcal{D}_1)$ is another value function. $D_1(\bar{y}|y)$ is the probability for the discriminator to correctly judge a real sample as sample drawn from the real distribution. $G_1(y)$ generates a sample from the model distribution condition on a known sample y~P(Y), the data prior distribution. $D_1(G_1(y))$ is the probability for the discriminator to wrongly judge a fake sample as a sample drawn from the real distribution. $1-D_1(G_1(y))$ is the probability for the discriminator to correctly judge a fake sample as a sample drawn from the generated distribution.

For a given $\mathcal{D}_1$, the optimal $\mathcal{G}_1$ is learned to maximally deceive $\mathcal{D}_1$ and for a given $\mathcal{G}_1$, the optimal $\mathcal{D}_1$ is learned to maximally judge real samples, generally, as many as possible. Theoretical results show that the optimization of value function defined in Eqn. 21 is equivalent to minimize the Jensen-Shannon divergence (JSD) between the underlying distribution, $P(\bar{Y}|Y)$ and model distribution, $Q(\bar{Y}|Y; G_1)$: $JSD\{P(\bar{Y}|Y)\|Q(\bar{Y}|Y; G_1)\}$.

To approximate the underlying domain transform process, a process similar to the previous case can be used. That is, the optimal mappings, $\mathcal{G}_2$ and $\mathcal{D}_2$ can be learned by optimizing the following cost function:

$$\min_{G_1} \max_{D_1} V(G_2, D_2) = E_{x \sim P(X)}[D_2^2(x)] + E_{\bar{y} \sim P(\bar{Y})}[(1 - D_2(G_2(\bar{y})))^2] \quad (22)$$

where, $V(\mathcal{G}_2, \mathcal{D}_2)$ is another value function. $\mathcal{D}_2(x)$ is the probability for the discriminator to correctly judge a real sample as a sample drawn from the real distribution. $G_2(\bar{y})$ generates a sample from the model distribution taking the output of previous generator $\mathcal{G}_1$ as its input. $D_2(G_2(\bar{y}))$ is the probability for the discriminator to wrongly judge a fake sample as a sample drawn from the real distribution. $1-D_2(G_2(\bar{y}))$ is the probability for the discriminator to correctly judge a fake sample as a sample drawn from the generated distribution. The optimization of value function defined in Eqn. 22 is equivalent to minimize the JSD between the underlying distribution, $P(X|\bar{Y})$ and model distribution, $Q(X|\bar{Y}; G_2)$: $JSD\{P(X|\bar{Y})\|Q(X|\bar{Y}; G_2)\}$.

Pre-training can also be used for the GAN in the robust domain transform/image reconstruction stage. Samples generated from the backprojection layer can be used as inputs. FBP reconstructed images of projection data simulated at standard dose level from monochromatic x-ray spectrum can be used as outputs. Glorot uniform distribution was used to initialize weights and zeros were used to initialize biases. Fifty full epoch was used as empirical stopping criterion. Batch size was fixed as 500. There were 86K samples for training the GAN. Learned parameters can then be used as initialization in fine tuning phase.

To make the trained network as generalizable as possible, projection datasets can include human anatomy as diverse as possible at different dose levels. Such datasets can be very difficult to obtain in large quantities using experimental or clinical data acquisition systems, as described above. However, simulation-based training datasets generation may not accurately represent the scanner-specific or data acquisition-related properties, such as polychromatic effects, scatter effects, bowtie filter, finite focal spot or non-ideal detection procedure. As such, a simulation-based, pre-training and an experiment-based fine-tuning strategy may be used in light of the aforementioned concerns. In the fine-tuning phase, except for those layers considered as frozen layers, all other layers can be initialized from the pre-training and fine-tuned using experimental datasets.

An optimization algorithm can be used. Value functions can be optimized using the stochastic gradient descent techniques. Learn rates ($\gamma=0.001$), $\beta_1=0.9$, $\beta_2=0.999$, $\in=10^{-8}$ can be empirically fixed. For the optimization of non-convex problems, initializations, stopping criterion, and training batch size are important.

Generating training datasets can be done via numerical simulations when needed. In one non-limiting example, twenty human subjects were scanned using a cardiac protocol at a clinical standard dose level. DICOM images of these exams were collected and used to generate projection data via a ray-driven implementation of the cone-beam forward projection procedure. Projections with quantum noise were then produced by sampling from a Poisson distribution for each projection ray. Entrance photon number for 100% dose level is set to be $I_0=10^6$ per ray. Other low-dose datasets were generated using 25%, 10%, 5%, 1% of $I_0$. To incorporate the effect of electronic noise that may be significant at low exposure levels, Gaussian distributed random values were added into the projection data before log-transform. The standard deviation of the electronic noise was adjusted to 20 photons per ray. Imaging geometry used to generate datasets can mimic a particular scanner. These simulated datasets were extensively used for pre-training purpose.

Scanner-specific properties can be further learned using physical phantom studies. In one non-limiting example, multiple repeated scans were performed on a quality assurance phantom and the GE HD 750 system. The phantom including seven inserts with different attenuation levels was measured from a combined set of 10 exposure levels (from 4 mAs to 280 mAs) at 80 kVp tube potential, with each parameter set repeated 50 times. These measurements were finally compared to a reference consisting of the average of an ensemble of 50 scans obtained at a reference dose level. After pre-training the network using simulated datasets, physical phantom datasets acquired at 4 mAs (fine-tuning inputs) and ensemble reference dose level (fine-tuning outputs) were used to fine-tune the pre-trained network. Scanner-specific properties could be learned and remembered in the network after the fine-tuning step.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for reconstructing an image of a subject acquired using a tomographic imaging system, the system comprising:
at least one computer processor configured to form an image reconstruction pipeline at least comprising:
a) an automated data correction module configured to receive imaging data acquired from the subject using ionizing radiation generated by the tomographic imaging system and generate corrected data using a first learning network;
b) an intelligent reconstruction module configured to receive at least one of the imaging data or the corrected data and reconstruct the image of the subject using a second learning network; and
a display configured to display the image of the subject.

2. The system of claim 1 wherein layers within at least one of the first learning network or the second learning network are designed to combine features from early layers together with features from late layers to form an input for later layers.

3. The system of claim 1 wherein the data correction module and the intelligent reconstruction module are formed using a multi-stage cascaded network architecture.

4. The system of claim 3 wherein the multi-stage cascaded network architecture includes a convolutional network stage configured to learn domain transform mapping, $\mathcal{F}$, which represents a relation between the ideal input data and transformed ideal projection data.

5. The system of claim 4 wherein domain transform stage includes a convolutional neural network trained on projection data before transformation to output of the domain transformation mapping, $\mathcal{F}$.

6. The system of claim 5 wherein the multi-stage cascaded network architecture includes a weighting stage configured to learn a single-view backprojection mapping $\mathcal{B}$.

7. The system of claim 6 wherein the multi-stage cascaded network architecture includes a rotational stage configured to determine a rotational mapping $\mathcal{R}$.

8. The system of claim 7 wherein the rotational stage is configured to combine contributions from all view angles in a beam mapping $\mathcal{D}$ into a target image volume with a linear activation function to generate the image of the subject.

9. The system of claim 8 wherein the domain transform stage, the pre-processing stage, the weighting stage, and the rotational stage are configured to learn the domain transform mapping $\mathcal{F}$, beam mapping $\mathcal{D}$, backprojection mapping $\mathcal{B}$, and rotation mapping $\mathcal{R}$, respectively, by the individually optimizing each stage using a shared optimization function.

10. The system of claim 1 further comprising a virtual radiologist module configured to shred the imaging data for training or to assess clinical usefulness of the image of the subject.

11. The system of claim 1 further comprising a virtual radiologist module to classify the input image into the unacceptable image or an acceptable image.

12. The system of claim 11 wherein the virtual radiologist module is configured to be shred images into sub-images for training.

13. A computed tomography (CT) system comprising:
an x-ray source and associated detectors configured to acquire imaging data from a subject over a range of view angles;
a computer system including at least one processor configured to operate as:
i) an automated correction module configured to receive imaging data acquired from the subject using the x-ray source and associated detectors and generate corrected data using a first learning network;
ii) an intelligent reconstruction module configured to receive at least one of the imaging data or the corrected data and reconstruct an image of the subject using a second learning network; and
a display configured to display the image of the subject.

14. The system of claim 13 wherein layers within at least one of the first learning network or the second learning network are designed to combine features from early layers together with features from late layers to form an input for later layers.

15. The system of claim 13 wherein the correction module and the intelligent reconstruction module are formed using a multi-stage cascaded network architecture.

16. The system of claim 15 wherein the multi-stage cascaded network architecture includes a domain transform stage configured to learn a projection data domain transform mapping, $\mathcal{F}$, which represents a relation between ideal projection data and filtered ideal projection data.

17. The system of claim 16 wherein domain transform stage includes a convolutional neural network trained on projection data without domain transform to generate domain transform mapping, $\mathcal{F}$, as an output.

18. The system of claim 17 wherein the multi-stage cascaded network architecture includes a weighting stage configured to learn a single-view backprojection mapping $\mathcal{B}$.

19. The system of claim 18 wherein the multi-stage cascaded network architecture includes a rotational stage configured to determine a rotational mapping $\mathcal{R}$.

20. The system of claim 19 wherein the rotational stage is configured to combine contributions from all view angles in a beam mapping $\mathcal{D}$ into a target image volume with a linear activation function to generate the image of the subject.

21. The system of claim 13 further comprising a virtual radiologist module configured to shred the imaging data for training or to assess clinical usefulness of the image of the subject.

22. A computed tomography (CT) system comprising:
- an x-ray source and associated detectors configured to acquire imaging data from a subject over a range of view angles;
- a computer system including at least one processor configured to operate as:
  - i) an automated correction module configured to receive imaging data acquired from a subject using the x-ray source and associated detectors and generate corrected data using a first learning network;
  - ii) a reconstruction module configured to receive the corrected data and reconstruct an image of the subject using at least the corrected data; and
- a display configured to display the image of the subject.

23. The system of claim 22 wherein the reconstruction module include is configured to reconstruct an image of the subject using at least one of a backprojection reconstruction process or a second learning network.

* * * * *

UNITED STATES PATENT AND TRADEMARK OFFICE
CERTIFICATE OF CORRECTION

PATENT NO. : 11,062,489 B2
APPLICATION NO. : 16/275129
DATED : July 13, 2021
INVENTOR(S) : Guang-Hong Chen et al.

It is certified that error appears in the above-identified patent and that said Letters Patent is hereby corrected as shown below:

In the Specification

Column 1, Line 18, "EB021183 and EB020521 awarded" should be -- EB021183 awarded --.

Signed and Sealed this
Eleventh Day of January, 2022

Drew Hirshfeld
*Performing the Functions and Duties of the
Under Secretary of Commerce for Intellectual Property and
Director of the United States Patent and Trademark Office*